United States Patent [19]
Baldus et al.

[11] Patent Number: 6,008,019
[45] Date of Patent: Dec. 28, 1999

[54] PLASMINOGEN ACTIVATOR FROM SALIVA OF THE VAMPIRE BAT

[75] Inventors: Berthold Baldus; Peter Donner; Wolf-Dieter Schleuning, all of Berlin, Germany; Alejandro Alagon, Mor., Mexico; Werner Boidol, Berlin, Germany; Jörn Reiner Krätzschmar, Berlin, Germany; Bernard Jacques Haendler, Berlin, Germany; Gernot Langer, Berlin, Germany

[73] Assignee: Schering Aktiengesellschaft, Berlin, Germany

[21] Appl. No.: 08/456,833

[22] Filed: Jun. 1, 1995

Related U.S. Application Data

[63] Continuation of application No. 08/197,582, Feb. 17, 1994, abandoned, which is a continuation of application No. 07/479,427, Feb. 13, 1990, abandoned.

[30] Foreign Application Priority Data

Feb. 13, 1989 [DE] Germany ............................. 39 04 580
May 30, 1989 [DE] Germany ............................. 39 17 949

[51] Int. Cl.$^6$ ............................. C12N 9/64; C12N 15/12; C12N 1/21; C12N 5/10
[52] U.S. Cl. .................... 435/69.2; 424/94.64; 435/69.1; 435/212; 435/226; 435/252.3; 435/320.1; 435/325; 536/23.2
[58] Field of Search .................. 435/226, 69.1, 435/69.2, 212, 252.3, 320.1, 325; 424/94.64; 536/23.2

[56] References Cited

U.S. PATENT DOCUMENTS

| | | | |
|---|---|---|---|
| 4,766,075 | 8/1988 | Goeddel et al. | 435/369 |
| 5,010,002 | 4/1991 | Levinson et al. | 435/69.2 |

FOREIGN PATENT DOCUMENTS 0 352 119  1/1990  European Pat. Off. .

OTHER PUBLICATIONS

Cartwright, Blood, vol. 43, No. 3, pp. 317–326 (1974).
Hawkey, Nature, vol. 211, pp. 434–435 (1966).
DiSanto, J. Morphol., vol. 106, pp. 301–335 (1960).
Scopes, "Protein Purification", Springer Verlag, New York, 2nd edition, pp. 183–185 and 190–191 (1987).
van Zonneveld et al., Proc. Natl. Acad. Sc: USA 83: 4670–4674 (1986).
Gheysen et al., J. Biol. Chem. 262(24): 11779–11784 (1987).
Gething et al., The EMBO J. 7(9): 2731–2740 (1988).
Stump et al., J. Biol. Chem. 261(36): 17120–17126 (1986).

*Primary Examiner*—Johnny F. Railey, II
*Attorney, Agent, or Firm*—Millen, White, Zelano & Branigan, P.C.

[57] ABSTRACT

The present invention relates to novel thrombolitic v-PA's which dissolve blood clots in the human body and thus are suitable for the treatment of cardial infarction, for example.

15 Claims, 37 Drawing Sheets

```
  1 GGCGCTGAAGCCCTGCAAGAGCTGAGCTGACGGGAAATCCTCTCCAGGAGAGAAGGAAGG  60

61 CAAGGAGTGGCGAGTTTAAGGGACACCCGCAGAAATGGTGAATACAATGAAGACAAAGCTG 120
                              M  V  N  T  M  K  T  K  L

121 TTGTGTGTACTGCTGCTTTGTGCTTTGTGGAGCAGTCTTCTCGTTGCCCAGGCAGGAACCTACAGG 180
     L  C  V  L  L  L  C  G  A  V  F  S  L  P  R  Q  E  T  Y  R

181 CAATTGGCAAGGGGATCCAGAGACATATGGTGTGGCCTGCAAAGACGAAATAACCCAGATG 240
     Q  L  A  R  G  S  R  A  Y  G  V  A  C  K  D  E  I  T  Q  M

241 ACATACCGGCGACAAGAGTCGTGGCTGCGCCCCGAGGTCAGAAGCAAGCGGGTGGAACAC 300
     T  Y  R  R  Q  E  S  W  L  R  P  E  V  R  S  K  R  V  E  H

301 TGCCAGTGCGATAGAGGCCAGGCCCGGTGCCAACACCGTGCCCGTCAACAGTTGCAGTGAA 360
     C  Q  C  D  R  G  Q  A  R  C  Q  H  T  V  P  V  N  S  C  S  E

361 CCAAGGTGCTTCAATGGGGGACATGCTGGCAGGTCTGTATATTTCTCAGACTTTGTCTGT 420
     P  R  C  F  N  G  G  T  C  W  Q  A  V  Y  F  S  D  F  V  C

421 CAGTGCCCTGCAGGATATACGGGGAAACGGTGTGAAGTAGATACCCGTGCCACCTGCTAT 480
     Q  C  P  A  G  Y  T  G  K  R  C  E  V  D  T  R  A  T  C  Y

481 GAGGGCCAGGGTGTCACCTACAGGGAGACATGAGCAGCAGAAGTAGGTTGAGTGT 540
     E  G  Q  G  V  T  Y  R  G  T  W  S  T  A  E  S  R  V  E  C

541 ATCAACTGGAACAGCAGCCTTCTGACCCGGAGACTTACAATGGGCGGATGCCAGATGCC 600
     I  N  W  N  S  S  L  T  R  R  T  Y  N  G  R  M  P  D  A

601 TTCAACCTGGGCCTTGGGAATCACAATTACTGCAGAAACCCAAATGGAGCCCCAAAACCT 660
     F  N  L  G  L  G  N  H  N  Y  C  R  N  P  N  G  A  P  K  P

661 TGGTGCTATGTCATCAAGGCAGGAAGTTCACTTGCTCGGAGTCCTGTAGCGTGCCTGTCTGC 720
     W  C  Y  V  I  K  A  G  K  F  T  S  E  S  C  S  V  P  V  C
```

FIG. 18A-1

```
721  TCCAAGGCCACTGTGGCCTGAGAAAGTACAAGGAGCCACAGCTTCACAGTACAGGAGGA 780
      S   K   A   T   C   G   L   R   K   Y   K   E   P   Q   L   H   S   T   G   G
781  CTCTTCACAGACATCACCTCTCATCCATGGCAGGCTGCCATCTTTGCCCAGAACAGAAGG 840
      L   F   T   D   I   T   S   H   P   W   Q   A   A   I   F   A   Q   N   R   R
841  TCATCAGGAGAGAAAGTTCTTGTGTGGGGGATATTGATCAGTTCCTGCTGGGTCCTGACT 900
      S   S   G   E   R   F   L   C   G   G   I   L   I   S   S   C   W   V   L   T
901  GCTGCCCACTGCTTCCAGGAGAGCTATCTTCCTGACCAGCTTAAGGTGGTTTTGGGCAGA 960
      A   A   H   C   F   Q   E   S   Y   L   P   D   Q   L   K   V   V   L   G   R
961  ACATACCGGGTGAAACCTGGAGAGGAAGAGCAGACATTTAAAGTCAAAAAATACATCGTC 1020
      T   Y   R   V   K   P   G   E   E   Q   T   F   K   V   K   K   Y   I   V
1021 CATAAGGAATTTGATGACGACACTTACAACAATGACATTGCACTGCTGCAGCTGAAAATCG 1080
      H   K   E   F   D   D   D   T   Y   N   N   D   I   A   L   L   Q   L   K   S
1081 GACTCACCACAGTGTGCCCAAGAGAGTGACAGTGTCCGCGCCATCTGTCTCCCGGAAGCC 1140
      D   S   P   Q   C   A   Q   E   S   D   S   V   R   A   I   C   L   P   E   A
1141 AACCTGCAGCTGCCCGACTGGACAGAATGTGAGCTGTCTGGCTACGGCAAGCATAAGTCA 1200
      N   L   Q   L   P   D   W   T   E   C   E   L   S   G   Y   G   K   H   K   S
1201 TCTTCTCCTTTCTATTCTGAGCAGCTGAAGGAAGGGCATGTCAGGCTGTACCCCTCCAGC 1260
      S   S   P   F   Y   S   E   Q   L   K   E   G   H   V   R   L   Y   P   S   S
1261 CGCTGCGCACCCAAGTTTCTGTTTAACAAAACCGTCACAAACAACATGCTGTGTGCTGGA 1320
      R   C   A   P   K   F   L   F   N   K   T   V   T   N   N   M   L   C   A   G
1321 GACACGCGGAGCGGAGAGATCTATCCAAATGTGCACGATGCCTGCCAGGGTGACTCAGGA 1380
      D   T   R   S   G   E   I   Y   P   N   V   H   D   A   C   Q   G   D   S   G
```

FIG. 18A-2

```
1381 GGCCCCTTGGTGTGTATGAATGACAACCACATGACTTTGCTTGGCATCATCAGTTGGGGT 1440
     G  P  L  V  C  M  N  D  N  H  M  T  L  L  G  I  S  W  G
1441 GTTGGCTGTGGGGAGAAAGACGTTCCAGTGTATACACCAAGGTTACTAATTACCTAGGC 1500
     V  G  C  G  E  K  D  V  P  G  V  Y  T  K  V  T  N  Y  L  G
1501 TGGATTCGAGACAACATGCACCTGTAACCAAGAACACACAACTCCCTGGCAGCCCCTGCC 1560
     W  I  R  D  N  M  H  L
1561 TTCCTCCAGCCCAGAAACACAAGGCAGAATGCTTCCTGACACCAGTTTCTCCACAAG 1620
1621 CCTGCACACAGTACTAGTGGGGGAGAACGTATAGGAGAGGGAGAGGGTATACTTCCAC 1680
1681 AGGTACTTCCCACTTCATAAGTTTTCAGGGATAAGGTCTGATTTAGAATCCATTTCTGT 1740
1741 CAGACAAGAAGACAGATAAATGCCAACCCCTCCCAGAACACCATCTAGGGCAGACAA 1800
1801 GAGGTAGAATAAAAGCCCAACTCCCTAATCTGTCAACATGAGCAGCTTTGGAAATGGGAC 1860
1861 CACCAAGATGAAAGTATCTTTCTAGTAAAAATAGCTAGATCCTTCAGTAAAGAAGTATC 1920
1921 ACATTAGAAATAAAATGTCCATGTATAGTCACAAGGACGCCCAACAGCGACCTGGCCTC 1980
1981 CTAACAAGGAATGGGCTGTCTGGCCAGATTGCGTTCCTCAGGCCATCCTTTGTACAGTATAAATCTTTTG 2040
2041 ACTATCCTCTTTCTACAGCTCTTGGAAGGAATTCCTTTTGTGTACAGTATAAATCTTTTT 2100
2101 CCTTTATAAACTTTATAGTAGAAGAACTGTATCATTCTGATAATCTGCTAAACTAGGCTTT 2160
2161 AGCATTTGATATCAATCCATTGTAGTTGCCACGACTCTGTATTATACTACACTGGAAAA 2220
2221 ATAAAATTCAGGCATATTTTTCACTTAAAAAAAA 2252
```

```
  1 GCCCTGCAAGAGCTGAGCTGACGGGAAATCCTCTCCAGGAGAGAAGGAAGCAAGGAGTG  60

61 GCGAGTTTAAGGACACCCGCAGAAATGGTGAATACAATGAAGACAAAGCTGTTGTGTGTA 120
                     M  V  N  T  M  K  T  K  L  L  C  V

121 CTGCTGCTTTGTGGAGCAGTCTTCTCGTTGCCCAGGCAGGAAACTACAGGCAATTGGCA 180
     L  L  L  C  G  A  V  F  S  L  P  R  Q  E  T  Y  R  Q  L  A

181 AGGGGATCCAGAGCATATGGTGTGCCGCCCCGAGGTCAGAGAGACGAAAAACCCAGATGATATACCAG 240
     R  G  S  R  A  Y  G  V  A  C  R  D  E  K  T  Q  M  I  Y  Q

241 CAACAAGAGTCGTGGCTGCGCCCCGAGGTCAGAGAAGCAAGCGGGTAGAACACTGCCGGTGC 300
     Q  Q  E  S  W  L  R  P  E  V  R  S  K  R  V  E  H  C  R  C

301 GATAGAGGATTGGCCCAGTGTCACACCGTGCCTGTCAAAGTTGCAGTGAACTGAGGTGC 360
     D  R  G  L  A  Q  C  H  T  V  P  V  K  S  C  S  E  L  R  C

361 TTCAATGGGGGACATGCTGCAGGCTGCATCTTTCTCAGACTTTGTCTGTCAGTGCCCT 420
     F  N  G  G  T  C  W  Q  A  A  S  F  S  D  F  V  C  Q  C  P

421 AAAGGATATACGGGGAAACAGTGTGAAGTAGATACCCATGCCACCTGCTACAAGGACCAG 480
     K  G  Y  T  G  K  Q  C  E  V  D  T  H  A  T  C  Y  K  D  Q

481 GGTGTCACCTACAGGGCACATGGAGCACATCGGAAAGTGGGGCTCAGTGTATCAACTGG 540
     G  V  T  Y  R  G  T  W  S  T  S  E  S  G  A  Q  C  I  N  W

541 AACAGCAACCTTCTGACCCGGAGGACTTACAATGGCCGGAGGTCAGATGCCATCACACTG 600
     N  S  N  L  L  T  R  R  T  Y  N  G  R  R  S  D  A  I  T  L

601 GGCCTTGGGAATCACAATTACTGCAGAAACCCAGATAACAACTCAAAACCTTGGTGCTAT 660
     G  L  G  N  H  N  Y  C  R  N  P  D  N  N  S  K  P  W  C  Y
```

```
 661 GTCATCAAGGCAAGCAAGTTCATCTTTGGAGTTCTGTAGCGTGCCTGTCTGCCTCCAAGGCC  720
      V  I  K  A  S  K  F  I  L  E  F  C  S  V  P  V  C  S  K  A
 721 ACCTGTGGCCTGAGAAGTACAAGGAGCCACAGTTCACAGTACAGAGGAGACTCTTCACA    780
      T  C  G  L  R  K  Y  K  E  P  Q  L  H  S  T  G  G  L  F  T
 781 GACATCACCTCTCATCCATGGCAGGCTGCCATCTTTGCCCAGAACAGAAGGTCATCAGGA   840
      D  I  T  S  H  P  W  Q  A  A  I  F  A  Q  N  R  R  S  S  G
 841 GAAAGGTTCTTGTGTGGGGGATATTGATCAGTTCCTGCTGGGTCCTGACTGCTGCCCAC    900
      E  R  F  L  C  G  G  I  L  I  S  C  W  V  L  T  A  A  H
 901 TGCTTCCAGGAGAGGTATCCTCCCCAGCATCTTAGGGTGGTTTTGGGCAGAACATACCGG   960
      C  F  Q  E  R  Y  P  P  Q  H  L  R  V  V  L  G  R  T  Y  R
 961 GTGAAACCTGGAAAGGAAGAGCAGACATTTGAAGTCGAAAAATGCATCGTCCATGAGGAA  1020
      V  K  P  G  K  E  E  Q  T  F  E  V  E  K  C  I  V  H  E  E
1021 TTTGATGACGACACTTACAACAATGACATTGCACTGCTGCAGCTGAAATCGGGCTCGCCA  1080
      F  D  D  D  T  Y  N  N  D  I  A  L  L  Q  L  K  S  G  S  P
1081 CAGTGTGCCAAGCAGGAGAGTGACAGTGTCCGGGCCATCTGTCTCCCGGAAGCCAACCTGCAG 1140
      Q  C  A  Q  E  S  D  S  V  R  A  I  C  L  P  E  A  N  L  Q
1141 CTGCCCGACTGGACAGAATGTGAGCTGTCTGGCTACGGCAAGCATAAGTCGTCTTCTCCT  1200
      L  P  D  W  T  E  C  E  L  S  G  Y  G  K  H  K  S  S  S  P
1201 TTCTATTCTGAGCAGCTGAAGGAAGGGCATGTCAGGCTGTACCCCTCCAGCCGCTGCACA  1260
      F  Y  S  E  Q  L  K  E  G  H  V  R  L  Y  P  S  S  R  C  T
1261 TCGAAGTTTCTGTTTAACAAAACCGTCACAAACAACATGCTGTGTGCTGGAGACACGCGG  1320
      S  K  F  L  F  N  K  T  V  T  N  N  M  L  C  A  G  D  T  R
```

FIG. 18B-2

```
1321  AGCGGAGAGATCTATCCAAATGTGCACGATGCCTGCCAGGGTGACTCAGGAGGCCCCTTG 1380
       S  G  E  I  Y  P  N  V  H  D  A  C  Q  G  D  S  G  G  P  L

1381  GTGTGTATGAATGACAACCACATGACTTTGCTTGGCATCATCAGTTGGGGTGTTGGCTGT 1440
       V  C  M  N  D  N  H  M  T  L  L  G  I  I  S  W  G  V  G  C

1441  GGGGAGAAAGACATTCCAGGTGTATACACCAAGGTTACTAATTACCTAGGCTGGATTCGA 1500
       G  E  K  D  I  P  G  V  Y  T  K  V  T  N  Y  L  G  W  I  R

1501  GACAACATGCGCCCATAACCAAGAACACGCAACTCCCTGGCAGCCCCTGCCTTCCTCCAC 1560
       D  N  M  R  P

1561  CCCAGAAGAAACACAAGGCAGAATGCTTCCTGACACCAGTTTCTCCACAAGCCTGCACAC 1620

1621  AGTACTAGTGGGGGAGAACGTATAGGAGAGGGGAAAGGGTGTACTTCCACAGGTACTTC 1680

1681  CCACTTCATAAGTTTTCAGGGATAAGGTCTGATTAGAATCCATTTCTGTCAGACAAGA 1740

1741  AGACAGATAAATGCCAACCCTCCCAGAACACCATCTAGGCAGACAAGAGGTAGAA 1800

1801  TAAAAGCCCAACCTCCTAATCTGTCAACGTGAGCAGCTTTGGAAATGGGACCACCAAGAT 1860

1861  GAAAGTATCTTTCTAGTAAAAAATAGCTAGATCCTTCAGTAAAGAAGTATCACATTAGAA 1920

1921  ATAAAATGTCCATGTATAGTCACAAGGACACCCAACAGCGACCTGGCCTCCTAACAAGG 1980

1981  AATGGGCTGTCTGGCCAGATTGCGTTCCTCAGGCCATCCTTTAAGTATTTGACTACCCCC 2040

2041  TTTCTACAGCTTTTGGAAGAATTCCTTTTGTGTACAGTATAAATCTTTTTCCTTTATAA 2100

2101  ACTTTATAGTAGAAGAACTGTATCATTCTGATAACTGCTAAACTAGGCTTTAGCATTTTG 2160

2161  ATATCAATCCATTGTAGTTGCCACAACTCTGTATTATACTACACTGGAAAAATAAATTCA 2220

2221  GGCATATTTTCACTTAAAAAAAAAAAAAAAAAAAAAAAA 2257
```

```
  1 GGCCAAGGCTGTGCGGAGAGATTGGGCGCTGAAGCCCTGCAAGAGCTGAGCTGACGGGAAA         60

61 TCCTCTCCAGGAGAAGAAGGAAGCAAGGAGTGGCGAGTTAAGGACACCGCAGAAATGG         120
                                                          M  V

121 TGAATACAATGAAGACAAAGCTGTTGTGTACTGCTGCTTTGTGGAGCAGTCTTCTCGT         180
     N  T  M  K  T  K  L  L  C  V  L  L  C  G  A  V  F  S  L

181 TGCCCAGGCAGGAAACCTACAGGCAATTGGCAAGGGATCCAGAGCATATGGTGGTTGCA         240
     P  R  Q  E  T  Y  R  Q  L  A  R  G  S  R  A  Y  G  G  C  S

241 GTGAACTGAGGTGCTTCAATGGGGGACATGCTGGCAGGCTGCATCTTTCTCAGACTTTG         300
     E  L  R  C  F  N  G  G  T  C  W  Q  A  A  S  F  S  D  F  V

301 TCTGTCAGTGCCCTAAAGGATATACGGGGAAACAGTGTGAAGTAGATACCCATGCCACCT         360
     C  Q  C  P  K  G  Y  T  G  K  Q  C  E  V  D  T  H  A  T  C

361 GCTACAAGGACCAGGGTGTCACCTACAGGGGAGCACATGGAAGTGGGGCTC         420
     Y  K  D  Q  G  V  T  Y  R  G  T  W  S  T  S  E  S  G  A  Q

421 AGTGTATCAACTGGAACAGCAACCTTCTGACCCGGAGACCTACAATGGGCGGAGGTCAG         480
     C  I  N  W  N  S  N  L  L  T  R  R  R  T  Y  N  G  R  R  S  D

481 ATGCCATCACACTGGCCTTGGGAATCACAATTACTGCAGAAACCCAGATAACAACTCAA         540
     A  I  T  L  G  L  G  N  H  N  Y  C  R  N  P  D  N  N  S  K

541 AACCTTGGTGCTATGTCATCAAGGCAAGCAAGTTCATCTTGGAGTTCTGTAGCGTGCCTG         600
     P  W  C  Y  V  I  K  A  S  K  F  I  L  E  P  C  S  V  P  V

601 TCTGCTCCAAGGCCACCTGTGCCCTGAGAAAGTACAAGGAGCCACAGCTTCACAGTACAG         660
     C  S  K  A  T  C  G  L  R  K  Y  K  E  P  Q  L  H  S  T  G
```

FIG. 18C-2

```
 661 GAGGACTCTTCACAGACATCACCTCTCATCCATGCCAGGCTGCCATCTTTGCCCAGAACA  720
       G  L  P  T  D  I  T  S  H  P  W  Q  A  A  I  F  A  Q  N  R

721 GAAGGTCATCAGGAGAGAAAGGTTCTTGTGTGGGGCCGATATTGATCAGTTCCTGCTGGTCC  780
       R  S  S  G  E  R  P  L  C  G  G  I  L  I  S  C  W  V  L

781 TGACTGCTGCCCACTGCTTCCAGGAGAGTATCCTCCCAGCATCTTAGGTGTTTTGG  840
       T  A  A  H  C  F  Q  E  R  Y  P  P  Q  H  L  R  V  V  L  G

841 GCAGAACATACCGGGTGAAACCTGGAAAGGAAGAGCAGACATTTGAAGTCGAAAAATGCA  900
       R  T  Y  R  V  K  P  G  K  E  E  Q  T  F  E  V  E  K  C  I

901 TCATCCATGAGGAATTTGATGACGACACTTACAACAATGACATTGCACTGCTGCAGCTGA  960
       I  H  E  E  F  D  D  D  T  Y  N  N  D  I  A  L  L  Q  L  K

961 AATCGGGCTGCGCCACAGTGTGCCCAAGAGAGTGACAGTGTCCGCGCCATCTGTCTCCCGG 1020
       S  G  S  P  Q  C  A  Q  E  S  D  S  V  R  A  I  C  L  P  E

1021 AAGCCAACCTGCAGCTGCCCGACTGGACAGAATGTGAGCTGTCTGGCTACGGCAAGCATA 1080
       A  N  L  Q  L  P  D  W  T  E  C  E  L  S  G  Y  G  K  H  K

1081 AGTCGCTCTTCTCCTTTCTATTCTGAAGTTTCTGTTTCAGAGCAGCTTCAGGCTGTACCCCT 1140
       S  S  P  F  Y  S  E  Q  L  K  E  G  H  V  R  L  Y  P  S

1141 CCAGCCGCTGCACATCGAAGTTTCTGTTTAACAAACCGTCACAAACAACATGCTGTGTG 1200
       S  R  C  T  S  K  F  L  F  N  K  T  V  T  N  N  M  L  C  A

1201 CTGGAGACACGCGGAGCGGAGAGATCTATCCAAATGTGCACGATGCCTGCCAGGGTGACT 1260
       G  D  T  R  S  G  E  I  Y  P  N  V  H  D  A  C  Q  G  D  S

1261 CAGGAGGCCCCTTGGTGTGTATGAATGACAACCACATGACTTTGCTTGGCATCATCAGTT 1320
       G  G  P  L  V  C  M  N  D  N  H  M  T  L  L  G  I  I  S  W
```

FIG. 18C-3

```
1321 GGGGTGTTGGCTGTGTGGGGAGAAAGACATTCCAGGTGTATACACCAAGGTTACTAATTACC  1380
       G  V  G  C  G  E  K  D  I  P  G  V  Y  T  K  V  T  N  Y  L
1381 TAGGCTGGATTCGAGACAACATGCGCCCATAACCAAGAACACGCAACTCCCTGGCAGCCC    1440
       G  W  I  R  D  N  M  R  P
1441 CTGCCTTCCTCCACCCCAGAAGAAACACAAGGCAGAATGCTTCCTGACACCAGTTTCTCC    1500
1501 ACAAGCCTGCACACAGTACTAGTGGGGGAGAACGTATAGGAGAAAGGGGTGTACT         1560
1561 TCCACAGTACTCCCACTTCATAAGTTTTCAGGGGATAAGGTCTGATTTAGAATCCATT     1620
1621 TCTGTCAGACAAGAAGACAGATAAAATGCCAACCTCCCAGAACACCACCATCTAGGGCA    1680
1681 GACAAGAGGTAGAATAAAAGCCCAACCTCCTAATCTGTCAACGTGAGCAGCTTTGGAAAT  1740
1741 GGGACCACCAAGATGAAGAATGTATCTTTCTAGTAAAAAATAGCTAGATCCTTCAGTAAAGAA 1800
1801 GTATCACATTAGAAATAAAAATGTCCATGTATAGTCACAAGGACACCCAACAGCGACCTGG  1860
1861 GCCTCCTAACAAGGAATGGGCTGTCTGGCCAGATTGCGTTCCTCAGGCCATCCTTTAAGT   1920
1921 ATTTGACTACCCCTTTCTACAGCTTTTGGAAGGAATTCCTTTTGTGTACAGTATAAATC    1980
1981 TTTTTCCTTTATAAACTTTATAGTAGAAGAACTGTATCATTCGATAACTGCTAAACTAG    2040
2041 GCTTTAGCATTTGATATCAATCCATTGTAGTGCCACAACTCTGTATTATACTACACTG     2100
2101 GAAAAATAAATTCAGGCATATTTTCACTTAAAAAAAA  2137
```

FIG. 18D-1

```
  1 GCTACAGAGAAGCCCGCCCACTGTGGGCCACTGACCCCCACCCCCTGCTTTGAAATACAGG    60

61 GGAGGCCGAGGCTGTGCGGAGAGATTGGCGCTGAAGCCCTGAAGAGCTGAGCTGACGGG     120

121 AAATCCTCTCCAGGAGAGAAGGAAGGCAAGGAGTGGCGAGTTTAAGGGACACCGCAGAAA    180
                                                                 M

181 TGGTGAATACAATGAAGACAAAGCTGTTGTGTGTACTGCTGTGTGGAGCAGTCTTCT      240
     V  N  T  M  K  T  K  L  L  C  V  L  L  C  G  A  V  F  S

241 CGTTGCCCAGGCAGGAAACCTACAGGCAATTGGCAAGGGATCCAGAGCATATGGTGATC    300
     L  P  R  Q  E  T  Y  R  Q  L  A  R  G  S  R  A  Y  G  D  P

301 CCCATGCCACCTGCTACAAGGACCAGGGTGTCACCTACAGGGACACATGGAGCACATCGG    360
     H  A  T  C  Y  K  D  Q  G  V  T  Y  R  G  T  W  S  T  S  E

361 AAAGTGGGGCTCAGTGTATCAACTGGAACAGCAATCTTCTGATCCGGAGGACTACAATG    420
     S  G  A  Q  C  I  N  W  N  S  N  L  L  I  R  R  T  Y  N  G

421 GGCGGATGCCAGAGCCCTCAAGCTGGGCCTTGGGAATCACAATTACTGTAGAAACCCAG    480
     R  M  P  E  A  V  K  L  G  L  G  N  H  N  Y  C  R  N  P  D

481 ATGGAGCCTCAAAACCTTGGTGCTATGTCATCAAGGCAAGAAGTTCACCTCAGAGTCCT    540
     G  A  S  K  P  W  C  Y  V  I  K  A  R  K  F  T  S  E  S  C

541 GTAGCCGTGCCTGTCTGCTCCAAGGCCACCTGTGGCCTGAGAAGTACAAGGAGCCACAGC    600
     S  V  P  V  C  S  K  A  T  C  G  L  R  K  Y  K  E  P  Q  L

601 TTCACAGTACAGGAGACTCTTCACAGACATCACCCTCTCATCCATGGCAGGCTGCCATCT    660
     H  S  T  G  G  L  F  T  D  I  T  S  H  P  W  Q  A  A  I  F
```

```
 661 TTGCCCAGAACAGAAGGTCATCAGGAGAAAGTTCTTGTGTGGGGAATATTGATCAGTT   720
      A  Q  N  R  R  S  S  G  E  R  F  L  C  G  G  I  L  I  S  S

721 CCTGCTGGGTCCTGACTGCTGCCCACTGTAAHCFQERYPPQHLR                780
      C  W  V  L  T  A  A  H  C  F  Q  E  R  Y  P  P  Q  H  L  R

781 GGGTGGTTTTGGGCAGAACATACGGGTGAAACCTGGAAAGGAAGCAGACATTTGAAG   840
      V  V  L  G  R  T  Y  R  V  K  P  G  K  E  E  Q  T  F  E  V

841 TCGAAAAATGCATCGTCCATGAGGAATTGATGACGACACTTACAACAATGACATTGCAC  900
      E  K  C  I  V  H  E  E  F  D  D  D  T  Y  N  N  D  I  A  L

901 TGCTGCAGCTGAAATCGGGCTCGCCACAGTGTGCCCAAGAGAGTGACAGTGTCCGCGCCA  960
      L  Q  L  K  S  G  S  P  Q  C  A  Q  E  S  D  S  V  R  A  I

961 TCTGTCTCCCGAAGCCAACCTGCAGCTGCCCGACTGGACAGAATGTGAGCTGTCTGGCT 1020
      C  L  P  E  A  N  L  Q  L  P  D  W  T  E  C  E  L  S  G  Y

1021 ACGGCAAGCATAAGTCGTCTCTTCCTCCTTTCTATTCTGAGCAGCTGAAGGAAGGGCATGTCA 1080
      G  K  H  K  S  S  P  F  Y  S  E  Q  L  K  E  G  H  V  R

1081 GGCTGTACCCCTCCAGCCGCTGCACATCGAAGTTTCTGTTTAACAAAACCGTCACAAACA 1140
      L  Y  P  S  S  R  C  T  S  K  F  L  F  N  K  T  V  T  N  N

1141 ACATGCTGTGTGCTGGAGACACGCGGAGCGGAGAGATCTATCCAAATGTGCACGATGCCT 1200
      M  L  C  A  G  D  T  R  S  G  E  I  Y  P  N  V  H  D  A  C

1201 GCCAGGGTGACTCAGGAGGCCCCTTGGTTGTGTGTGGGGAGAAAGACATTCCAGGTGTATACACCAAGG 1260
      Q  G  D  S  G  G  P  L  V  C  M  N  D  N  H  M  T  L  L  G

1261 GCATCATCAGTTGGGGTGTTGGCGTGTGCGGAGAAAGACATTCCAGGTGTATACACCAAGG 1320
      I  I  S  W  G  V  G  C  G  E  K  D  I  P  G  V  Y  T  K  V

1321 TTACTAATTACCTAGGCTGGATTCGAGACAACATGCGCCCATAACCAAGAACACGCAACT 1380
      T  N  Y  L  G  W  I  R  D  N  M  R  P
```

```
1381 CCCTGGGAGCAGCCCCTGCCTTCCTCCACCCCAGAGAAACACAAGGCAGAATGCTTCCTGAC 1440
1441 ACCAGTTTCTCCACAAGCCTGCACACAGTACTAGTGGGGGAGAACGTATAGGAGAGGGG 1500
1501 AAAGGGTGTACTTCCACAGGTACTTCCCACTTCATAAGTTTTCAGGGGATAAGGTCTGAT 1560
1561 TTAGAATCCATTTCTGTCAGACAAGAAGACAGATAAATGCCAACCCCTCCCAGAACACCA 1620
1621 CCATCTAGGGCAGACAAGAGGTAGAATAAAAGCCCAACCTCCTAATCTGTCAACGTGAGC 1680
1681 AGCTTTGGAAATGGGACCACCAAGATGAAAGTATCTTTCTAGTAAAAATAGCTAGATCC 1740
1741 TTCAGTAAAGAAGTATCACATTAGAAATAAAATGTCCATGTATAGTCACAAGGACACCCA 1800
1801 ACAGCGACCTGGGCCCTCCTAACAAGGAATGGGCTGTCTCGGCCAGATTGCGTTCCTCAGGC 1860
1861 CATCCTTTAAGTATTTGACTACCCCCTTTCTACAGCTTTTGGAAGGAATTCCTTTTGTGT 1920
1921 ACAGTATAAATCTTTTCCTTTATAAACTTTATAGTAGAAGAACTGTATCATTCTGATAA 1980
1981 CTGCTAAACTAGGCTTTAGCATTTGATATCAATCCATTGTAGTTGCCACAACTCTGTAT 2040
2041 TATACTACACTGGAAAAATAAATTCAGGCATATTTTCACTTAAAAAAAAAAAAAAAAA 2100
```

FIG. 19A

```
1    GGCGCTGAAGCCCTGCAAGAGAGCTGAGCTGACGGGAAATCCTCTCCAGGAG    50
1    ..........................ACAGGGCTGGAGAGAAACCTCTGC...GAG    28
                                                              *
51   AGAAGGAAGGCAAGGAGTGGCGAGTTTAAGGACAC..CGCAGAAATGGT    98
29   GAAAGGGAAGGAGCAAGCCGTGAATTTAAGGACGCTGTGAAGCAATCAT    78
                                                              *
99   GAATACAATGAAGACAAAGCTGTTGTGTGTACTGCTGCTTTGTGGAGCAG    148
79   GGATGCAATGAAGAGAGGGCTCTGCTGTGTGCTGCTGTGTGGGAGCAG    128
                                                              *
149  TCTTCTCGTTGCCCAGGCAGGAAACCTACAGGCAATTGGCAAGGGGATCC    198
129  TCTTCGTTTCGCCCAGCCAGGAAATCCCGATTTCAGAAGAGGAGCC    178
                                                              *
199  AGAGCATATGGTGTGGCCTGCAAAGACGAAATAACCCAGATGACATACCG    248
179  AGATCTTACCAAGTGATCTGCAGAGATGAAAAACGCAGATGATATACCA    228
                                                              *
249  GCGACAAGAGTCGTGGCTGCGCCCCGAGGTCCAGAAGCAAGCGGGTGGAAC    298
229  GCAACATCAGTCAGTGGCACAGTGCTGCTCAGAAGCAACCGGGTGGAAT    278
                                                              *
299  ACTGCCAGTGCGATAGAGGCCAGGCCCGTGCCACACCGTGCCCGTCAAC    348
279  ATTGCTGGTGCAACAGTGGCAGGCACAGTGCCACTCAGTGCCTGTCAAA    328
                                                              *
349  AGTTGCAGTGAACCAAGGTGCTTCAATGGGGGACATGCTGGCAGGCTGT    398
329  AGTTGCAGCGAGCCAAGGTGTTTCAACGGGGGCACCTGCCAGCAGCCCT    378
```

```
717  ACTGCTACTTTGGGAATGGGTCAGCCTCAGCCTGGCACGGCACCAGCCTCACC   766
767  GAGTCGGGTGCCTCCTGCCTCCCGTGGAATTCCATGATCCTGATAGGCAA      816
817  GGTTTACACAGCACACAGAACCCCAGTGCCCAGGCACTGGGCCTGGGCAAAC    866
867  ATAATTACTGCCGGAATCCTGATGGGGATGCCAAGCCCCTGGTGCCACGTG     916
917  CTGAAGAACCGCAGGCTGACGTGGGAGTACTGTGATGTGCCCTCCTGCTC      966
967  CACCTGCG..........                                      974
                *                        *                      *
737  GCCTGAGAAGTACAAGGAGCCACAGCTTCACAGTACAGGAGGACTCTTC       786
975  GCCTGAGACAGTACAGCCAGCCTCAGTTTCGCATCAAAGGAGGGCTCTTC     1024
                *                        *                      *
787  ACAGACATCACCTCTCATCCATGGCAGGCTGCCATCTTTGCCCAGAACAG      836
1025 GCCGACATCGCCTCCCACCCTGGCAGGCTGCCATCTTTGCCAAGCACAG      1074
                *                        *                      *
837  AAGGTCATCAGGAGAGAAAGGTTCTTGTGTGGGGGATATTGATCAGTTCCT     886
1075 GAGGTCGCCCGGAGAGCGGTTCCTGTGCGGGGCATACTCATCAGCTCCT      1124
```

```
 887  GCTGGGTCCTGACTGCTGCCCACTGCTCTTCCAGGAGAGCTATCTTCCTGAC    936
1125  GCTGGATTCTCTGCCGCCCACTGCTCTTCCAGGAGAGGTTTCCGCCCCAC     1174
 937  CAGCTTAAGGTGGTTTGGGCAGAACATACCGGGTGAAACCTGGAGAGGA      986
1175  CACCTGACGGGTGATCTTGGGCAGAACATACCGGGTGGTCCCTGGCGAGGA    1224
 987  AGAGCAGACATTTAAAGTCAAAAAATACATCGTCCATAAGGAATTTGATG    1036
1225  GGAGCAGAAATTTGAAGTCGAAAAAATACATTGTCCATAAGGAATTCGATG    1274
1037  ACGACACTTACAACAATGACATTGCACTGCTGCAGCTGAAATCGGACTCA    1086
1275  ATGACACTTACGACAATGACATTGCGCTGCTGCAGCTGAAATCGGATTCG    1324
1087  CCACAGTGTGCCCAAGAGAGTGACAGTGTCCGCGCCATCTGTCTCCCGGA    1136
1325  TCCCGTGTGCCCAGGAGAGCAGCGTGTCCGCACTGTGTGCCTTCCCCC      1374
1137  AGCCAACCTGCAGCTGCCCGACTGGACAGAATGTGAGCTGTCTGGCTACG    1186
1375  GGCGGACCTGCAGCTGCCGGACGGAGTGAGCTGTCTCCGGCTACG         1424
1187  GCAAGCATAAGTCATCTTCCTTTCTATTCTGAGCAGCTGAAGGAAGGG      1236
1425  GCAAGCATGAGGCCTTGTCTCCTTTCTATTCGGAGCGGCTGAAGGAGGCT    1474
```

```
1237 CATGTCAGGCTGTACCCCTCCAGCCGCTGCGCACCCAAGTTTCTGTTTAA 1286
     ||||||||||||||||||||||||||||||||||||||| ||||||||||
1475 CATGTCAGACTGTACCCCATCCAGCCGCTGCACATCACAACATTTACTTAA 1524

1287 CAAAACCGTCACAAACAACATGCTGTGTGTGGAGACACGGGAGCGGAG 1336
     || |||| ||||| ||||||||||||||||| |||||| ||||| |||
1525 CAGAACAGTCACCGACAACATGCTGTGTGCTGGAGACACTCGGAGCGGGCG 1574

1337 AGATCTATCCAAATGTGCACGATGCCTGCCAGGGTGACTCAGGAGGCCCC 1386
     ||  ||| |||| ||||||| ||| ||||||||||||  ||||||||||
1575 GGCCCCAGGCAAACTTGCACGACGCCTGCCAGGGCGATTCGGGAGGCCCC 1624

1387 TTGGTGTGTATGAATGACAACCACAGACTTTGCTTGGCATCATCAGTTG 1436
     |||||||||  |||||   ||||||| ||||| |||||||||||||| |
1625 CTGGTGTGTCTGAACGATGGCCGCATGACTTTGGTGGGCATCATCAGCTG 1674

1437 GGGTGTTGGCTGTGGGAGAAAGACGTTCCAGTGTATACACCAAGGTTA 1486
     ||| ||||||||||||| |||||| ||||||||||  |||||||||||
1675 GGGCCTGGGCTGTGTGGACAGAAGGATGTCCCGGGTGTGTACACCAAGGTTA 1724

1487 CTAATTACCTAGGCTGGATTCGAGACAACATGCACCTGTAACCAAGAACA 1536
     | || ||| |||||||||||  |||| |||||| ||||||||||||||
1725 CCAACTACCTAGACTGGATTCGTGACAACATGCGACCGTGACCAGGAACA 1774

1537 CACAACTCCCTGGCAGC.........CCCTGCCTTCCTCCAGCCCAGAAG 1577
     || |||||| |||||||         ||| |||||| |||||||||| 
1775 CCCGACTCCCTCAAAAGCAAATGAGATCCCGCCCTCTCTTCAGAAGAC 1824

1578 AAACACAAGGCAGAATGCTTCCTGACACCAGTTTCTCCACAAGCCTGCAC 1627
     || ||||||| || ||||||||| || ||||| || ||||| ||||||
1825 ACTGCAAAGGCGCAGTGCGCTTCTCTACAGACTTCTCCAGAC....CCACCAC 1871
```

```
1628 ACAGTACTAGTGGGGGAGAACGTATAGGAGAGGGAGAGGGTATACTTC 1677
     ||  |||||| |||||||||||| |||||||| |||  || ||||||
1872 ACCGCAGAAGCGGGACGAGACCCTACAGGAGAGGGAAGAGTGCAT..TTT 1919

1678 CACAGGTACTTCCCACTTCATAAGTTTTCAGGGGATAAGGTCTGATTTAG 1727
     ||||||||||||||||||||||||||||||||    ||||||||||||||
1920 CCCAGATACTTCCCATTTTTGGAAGTTTTCA..GGACTTGGTCTGATTTCA 1967

1728 AATCCATTTCTGTCAGACAAGAAGACAGATAAATGCCAACCCCTCCCAGA 1777
     |||||||||||||||||||  |||| ||||||||||||||||||||||||
1968 GGATACTCTGTCAGATGGGAAGACATGAATGCCAACACTAGCCTCTCCAGGA 2017

1778 ACACCACCATCTAGGGCAG.........ACAAGAGGTAGAATAAAA 1814
     |||||||||||||||||||         |||||||||||||||||
2018 ATGCCTCCTCCCTGGGCAGAAGTGGCCATGCCACCCTGTTTTCAGCTAAA 2067

1815 GCCCAACCCTCCTAATCTGTCAACATGAGCAGCTTTGGAAATGGGACCACC 1864
     ||||||||||||||||||||||||||||||||||||||||||||||||||
2068 GCCCAACCCTCCTGACCTGTCACCGTGAGCAGCTTTGGAAACAGGACCACA 2117

1865 AAGATGAAAGTATCTTTC..TAGTAAAAAAATAGCTAGATCCTTCAGTAAA 1912
     |||||||||||||||||  ||||||||||||||||||||||||||||||
2118 AAAATGAAAGCATGTCTCAATAGTAAAAGATAAACAAGATCTTTCAGGAAA 2167

1913 GAAGTATCACATTAGAAAATAAAATGTCCATGTATAGTCACAAGGACGCCC 1962
     ||||||||||||||||||||||||||||||||  |  ||||||| |||||
2168 GACGGATTGCATTAGAAATAGACAGTATATTTATAGTCACAAGAGCCCAG 2217

1963 AACAGCGACCTGGCCTCCTAACAAGGAATGGGCTGTCTGGCCAGATTGC 2012
     ||||||||||||||||||||         ||||||||||||||||
2218 CAGGGC.........TCAAAGTTGGGGCAGGCTGGCTGGCCCGTCATG 2256
```

```
2013 GTTCCTCAGGCCATCCTTTAAGT.......ATTTGACTATCCTCTTTCT 2054
     ||||||||||||||||||||||||      ||||||||||||||||||||
2257 TTCCTCAAAAGCACCCTTGACGTCAAGTCTCCCTTTCCCCACTCC 2306

2055 ACAGCTCTTGGAAGGAATTCCTTTTGTGTAC..........AGTATAAATC 2095
     ||||||||||||||||||||||||||||||          ||||||||||
2307 CTGGCTCTCAGAAGGTATTCCTTTTGTGTACAGTGTGTAAAGTGTAAATC 2356

2096 TTTTTCCTTTATAAACTTTATAGTAGAAGAACTGTATCATTCTGATAACT 2145
     ||||||||||||||||||||||||||||||||||||||||||||||
2357 CTTTTCTTTATAAACTTTAGAGTAGCATGA...GAGAATTGTATCATTT 2403

2146 GCTAAACTAGGCTTTAGCATTTGATATCAATCCATTGTA........... 2185
     |||||||||||||||||||||||||||||||||||||||
2404 GAACAACTAGGCTTCAGCATATTATAGCAATCCATGTTAGTTTTTACTT 2453

2186 ...GTTGCCACGACTCTGTATTATACTACACTGGAAAAATAAATTCAGGC 2232
        ||||||||||||||||||||||||||||||||||||||||||||||
2454 TCTGTTGCCACAACCCTGTTTTATACTGTACT....TAATAAATTCAGAT 2499

2233 ATATTTTCACTTAAAAAAA 2252
     |||||||||||||
2500 ATATTTTCACAGTTTTTCC 2519
```

PLASMINOGEN ACTIVATOR FROM SALIVA OF THE VAMPIRE BAT

This is a continuation of application Ser. No. 08/197,582 filed Feb. 17, 1994, now abandoned, which is a continuation of application Ser. No. 07/479,427 filed Feb. 13, 1990, also abandoned.

BACKGROUND OF THE INVENTION

The present invention relates to a novel thrombolytic, processes for its isolation, and its pharmaceutical usage.

Thromboses are produced by the formation of a blood clot in blood vessels. One distinguishes between venous thromboses including pulmonary embolisms and arterial thromboses including acute myocardial infarction.

Pulmonary embolism and cardiac infarction are life-threatening events requiring immediate medical intervention.

Besides various invasive methods, a popular form of therapy for arterial and venous thromboses has evolved in recent years in the form of enzymatic thrombolysis with plasminogen activators. These substances, called thrombolytics, convert plasminogen, the inactive proenzyme of the fibrinolysis system in the blood, into the active proteolytic enzyme,plasmin. Plasmin, in turn, dissolves the fibrous substance, fibrin, which is a substantial component of a blood clot; this leads to reopening of the blocked vessels and restoration of blood flow. However, plasmin is a relatively unspecific protease, i.e. once formed in the blood, it destroys,.by proteolysis, components in the blood indispensable for intact hemostasis (e.g. fibrinogen) and thereby induces under certain circumstances dangerous risks of hemorrhaging.

The thrombolytics of the first generation, streptokinase and urokinase, are compounds which, once injected into the circulation, systemically convert plasminogen into plasmin and induce systemic proteolysis. Therefore, thrombolysis therapies with these substances are frequently accompanied by complications due to hemorrhage. The fibrin-specific thrombolysis, developed thereafter, wherein recombined plasminogen activators of the tissue type, called t-PA for the sake of brevity, are employed, was supposed to lead out of this dilemma. In the blood circulation, t-PA has an only low affinity to plasminogen. However, in the presence of the fibrous substance, fibrin, with which it reacts by way of specific binding sites, this affinity is increased by a multiple, resulting in plasmin formation on the surface of the thrombus. This concept could be verified in vitro and in animal experiments; the clinical studies, however, show that large amounts of t-PA are needed in order to bring about rapid dissolution of a coronary thrombosis.

However, if doses of t-PA of such magnitude are infused, this will lead to a systemic proteolysis accompanied by a relative risk of hemorrhaging, in a similar way as in the cases of streptokinase and urokinase. Therefore, one speaks nowadays of a relative fibrin specificity of t-PA. The cause therefor lies in an essential characteristic of t-PA: This molecule is an active protease which, under favorable conditions (high enzyme concentration, long exposure time, high substrate concentration, optimal pH and ion environment), will convert plasminogen into plasmin even in the absence of fibrin. All of these conditions are met in present clinical standard therapy with t-PA.

SUMMARY OF THE INVENTION

During a search for more specific plasminogen activators fulfilling the criterion of fibrin specificity, a new, natural compound exhibiting fibrinolytic activity has been found, called v-PA.

The invention concerns the thrombolytically active agent v-PA from the saliva of bats of the genus Desmodus spec., distinguished by the following characteristic properties:

four different cDNA's were discovered from a salivary gland cDNA bank which code for four different v-PA proteins:

(1) v-PA $\alpha_1$: High-molecular form consisting of a finger domain, an EGF (epidermal growth factor) domain, a Kringel domain, and a protease domain (Example 18).

(2) v-PA $\alpha_2$: High-molecular form with the same domains as v-PA $\alpha_1$, but different from v-PA $\alpha_1$ in the nucleotide as well as amino acid sequence.

(3) v-PA $\beta$: Molecular form consisting of an EGF domain, a Kringel domain, and a protease domain (Example 18).

(4) v-Pa $\gamma$: Low-molecular form consisting of a Kringel domain and a protease domain.

The main protein band of the active agent v-PA $\alpha_1$ shows a molecular weight of 43,000±2,000 (Example 2), in a sodium dodecyl sulfate gel electrophoresis under non-reducing conditions.

The main protein band of the active agent v-PA $\beta$ shows a molecular weight of 39,000±3,000 in a sodium dodecyl sulfate gel electrophoresis under nonreducing conditions, and a molecular weight of 43,000±2,000 under reducing conditions (Example 1).

The activity of the active agent v-PA $\beta$ is eluted from a gel filtration column ("Superose" 12) with a molecular weight of 40,000±3,000 (Example 1).

The isoelectric points (pI) of the active agent v-PA $\beta$ range between 6.8 and 8.5.

The active agent reacts with $^3$H-diisopropyl fluorophosphate and thus is a serine protease (Example 9).

The active agents v-PA $\alpha_1$ and v-PA $\beta$ hydrolyze the chromogenic peptides: S-2288 (H-D-Ile-Pro-Arg-pNA) and S-2444 (<Glu-Gly-Arg-pNA), but not the chromogenic peptide S-2251 (H-D-Val-Leu-Lys-pNA) (Example 16).

The active agent does not bind to lysin "Sepharose" (Example 14) in a pH range of 4–10.5.

The active agents v-PA $\alpha_1$ and v-PA $\beta$ produce lysis halos on fibrin plates, but not on casein plates (Example 15).

The active agents v-PA $\alpha_1$ and v-PA $\beta$ bind, at a pH of 7.5, to $Zn^{++}$ chelate "Sepharose" (Examples 1 and 2).

The active agent v-PA a activates plasminogen only in the presence of stimulants, such as fibrin, but not in the presence of fibrinogen (Example 7).

The active agent v-PA $\beta$ does not follow the classical Michaelis-Menten kinetics in converting plasminogen into plasmin in the presence of fibrin monomers; v-PA $\beta$ is an enzyme having allosteric properties (Example 12).

The active agent lyses, in dependence on the concentration, human whole blood thrombi in vitro (Example 8).

In a reconstituted, clottable in vitro system, the active agent v-PA $\beta$ does not lead to a measurable fibrinogen degradation (Example 10), in contrast to t-PA.

In an in vitro fibrinolysis test (International Clot-Lysis Assay), the active agent causes fibrinolysis in dependence on the concentration (Example 13).

The active agents v-PA $\alpha_1$ and v-PA $\beta$ bind to heparin-"Sepharose" and can again be eluted therefrom by suitable solutions (Example 4).

The active agent binds to immobilized inhibitor which is isolated from the seeds of various Erythrina species and can again be separated therefrom by suitable solutions (Example 3).

The active agents v-PA $\alpha_1$ and v-PA $\beta$ bind to fibrin-"Celite" and can be eluted again by suitable methods (Example 5).

The active agent binds to hydroxyapatite under certain conditions and cap be eluted again with a phosphate-containing buffer (Example 2).

The active agents v-PA $\alpha_1$ and v-PA $\beta$ can be separated from each other and isolated by suitable methods (Examples 2, 4, and 5).

The active agents v-PA $\alpha_1$ and v-PA $\beta$ differ from each other with regard to their N-terminal amino acid sequence (Example 6).

reference herein. The v-PA in its form not binding to fibrin has a molecular weight of 38.000±2.000.

By substantially pure is meant that a protein is purified, e.g. to a degree that its activity is enhanced significantly over that of the protein in nature. Preferably, the protein will be purified to homogeneity and most preferably will be at least 90%, especially greater than 95% pure or higher.

The DNA sequences of this invention can be routinely inserted into the common, e.g., commercially availably, vectors such as plasmids, phages etc. useful for expression in, e.g., the common, e.g., commercially available cell lines.

Oligonuclootide probes specific for v-PA sequences will be constructed routinely by selecting sequences in the leader region or the complete sequence which are different from t-PA (see comparison in FIG. 19).

```
vPA-β  141 CTGTTGTGTGTACTGCTGCTTTGTGGAGCAGTCTTCTCGTTGCCCAGGCA 190
           || |  ||||| ||||||||| ||||||||||||||||   | |||||| ||
t-PA    98 CTCTGCTGTGTGCTGCTGCTGTGTGGAGCAGTCTTCGTTTCGCCCAGCCA 147 vPA-β  191 GGAAACCTACAGGCAATTGGCAAGGG 216
           ||||| | |    | |||   ||| |
t-PA   148 GGAAATCCATGCCCGATTCAGAAGAG 173
```

The active agents v-PA $\alpha_1$ and v-PA $\beta$ differ with respect to their amino acid and nucleotide sequence (Example 18).

The coding sequence of the active agents can be incorporated into a corresponding vector "septan". These express the active agent in suitable eukaryotic cell systems (Example 19).

The thrombolytic active agent v-PA represents a novel, naturally occurring plasminogen activator which dissolves blood clots in the human body and thus is suitable for treatment of, for example, cardiac infarction.

This agent is found in the saliva of all species of bats of the genus Desmodus spec. in low concentrations and is probably expressed by the cells of the salivary glands of this type of animal. The bats of the genus Desmodus spec. encompass all kinds of bats of the American continent. The genus Desmodus of Central America and Mexico has been the subject of especially thorough investigation.

The invention also relates to several methods for the isolation of the thrombolytic v-PA from the saliva of Desmodus spec. according to claim 9, characterized in that the centrifuged saliva is taken up in a buffer, chromatographed over a $Zn^{++}$ chelate "Sepharose" column, the active agent v-PA is quantitatively eluted after washing of the column, the collected fractions are filtered in the absense of salts over "Superose" 12, and finally are again subjected to gel filtration in the presence of a physiological saline solution. The exact process parameters have been set forth in Example 1.

The invention furthermore concerns medicinal agents based on the compound v-PA, as well as conventional auxiliary agents and excipients.

The superiority of the novel thrombolytic v-PA as compared with t-PA can be derived from Examples 7, 8, 10 and 15 set forth below.

It is preferred that there is administered a combination of v-PA in its form not binding to fibrin and a plasminogen-activator (binding to fibrin), e.g., urokinase, prourokinase (scu-PA), t-PA and the higher molecular form of the thrombolyticum v-PA with a molecular weight of 43.000±2.000, as described in the Federal Republic of Germany application P 39 43 241.6 of Dec. 22, 1989, which is incorporated by Shown above are the DNA sequences of the probe used for screening of the cDNA library derived from clone vPA$_\beta$ by digestion with restriction endonucleases BamHI and AluI (vPA$_\beta$) and the corresponding sequence from a t-PA cDNA clone (t-PA).

Antibodies can also be routinely prepared by normal methods, e.g., by raising them in animals such as goats.

The v-PA of this invention can be administered to mammals, including humans, analogously to the use of the t-PA but with fewer side effects due to the selectivity of v-PA as discussed above. In general, lower doses than otherwise needed for t-PA may be employable. Suitable activities can be routinely determined by employing conventional protocols. Typical indications include those for which thrombolytics are useful, e.g., cardiac infarct, stroke, arterial thrombosis, etc. The usual galenic additives can be employed to produce pharmaceutical formulations.

BRIEF DESCRIPTION OF THE DRAWINGS

Various other objects, features and attendant advantages of the present invention will be more fully appreciated as the same becomes better understood when considered in conjunction with the accompanying drawings, and wherein:

FIG. 18(A) represents a complete DNA sequence of the cDNA insert of the longest found plasmid clone of the group $\alpha_1$ with derived amino acid sequence; the coding sequence begins with nucleotide 94 (ATG . . . ) and ends with the stop codon at nucleotide 1527 ( . . . TAA); the derived amino acid sequence is indicated in the single-letter code, each amino acid standing under the first nucleotide of the triplet by which it is coded;

FIG. 18(B) represents a complete DNA sequence of the cDNA insert of type $\alpha_2$ with derived amino acid sequence; the coding sequence begins with nucleotide 85 (ATG . . . ) and ends with the stop codon at nucleotide 1518 ( . . . TAA); the derived amino acid sequence is indicated in single letter code, each amino acid standing under the first nucleotide of the triplet by which it is coded;

FIG. 18(C) represents the complete DNA sequence of the cDNA insert of the longest found plasmid clone of the group $\beta$ with derived amino acid sequence; the coding sequence begins with nucleotide 117 (ATG . . . ) and ends with the stop codon at nucleotide 1412 ( . . . TAA); the derived amino acid sequence is indicated in the single-letter code, each amino acid standing under the first nucleotide of the triplet by which it is coded;

FIG. 18(D) represents the complete DNA sequence of the cDNA insert of the plasmid clone of the type γ with derived amino acid sequence; the coding sequence begins with nucleotide 180 (ATG . . . ) and ends with the stop codon at nucleotide 1364 ( . . . TAA); the derived amino acid sequence is indicated in single letter code, each amino acid standing under the first nucleotide of the triplet by which it is coded;

Figure 19B:
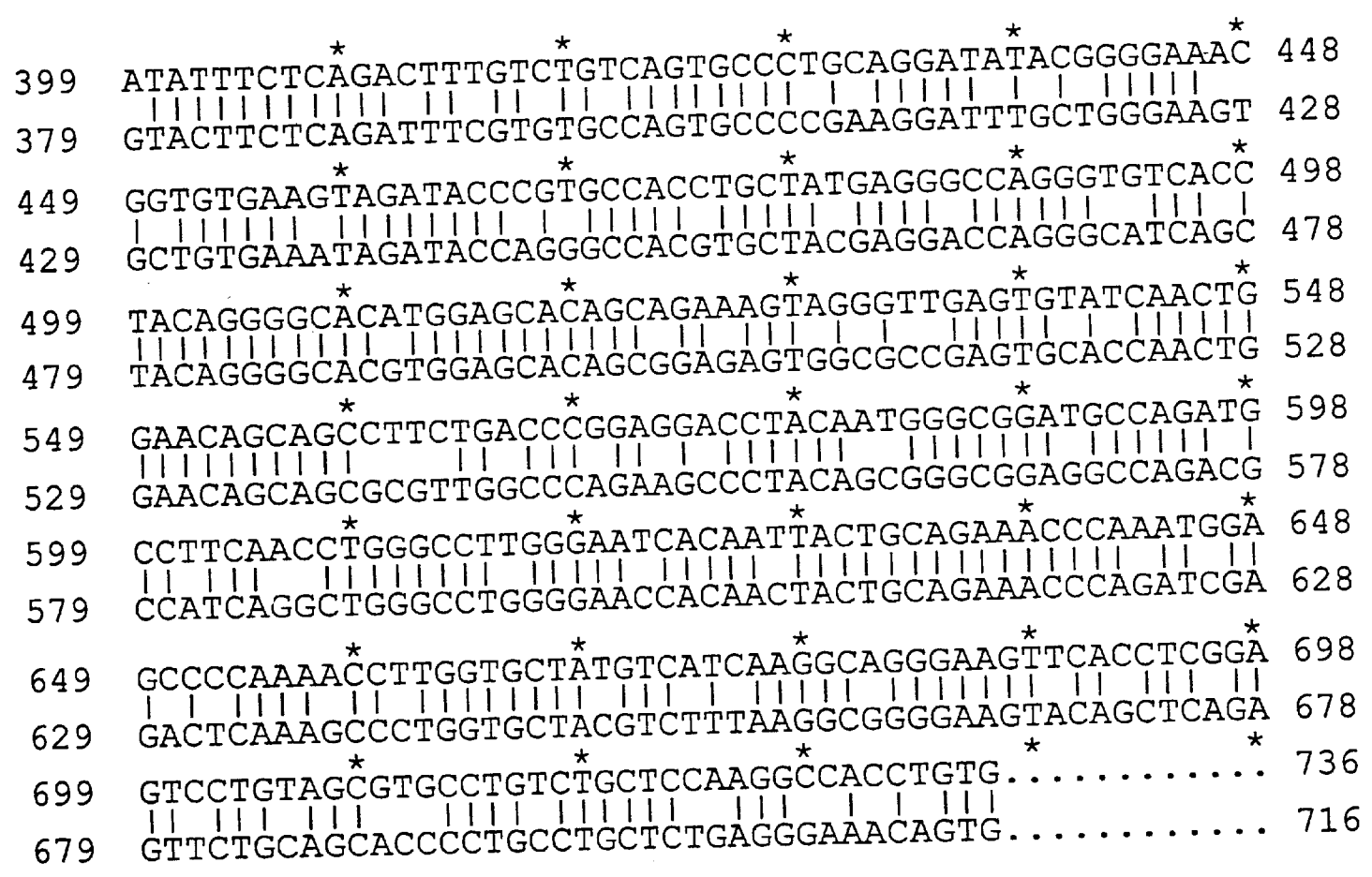

FIG. 19 represents a comparison of the v-PA $\alpha_1$ cDNA sequence (upper line of the alignment) with that of t-PA (lower line)

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding applications Federal Republic of Germany Appln. Serial No. P 39 04 580.3, filed Feb. 13, 1989 and Federal Republic of Germany Appln. Serial No. P 39 17 949.4, filed May 30, 1989, are hereby incorporated by reference.

EXAMPLES

Example 1

Figure 1:
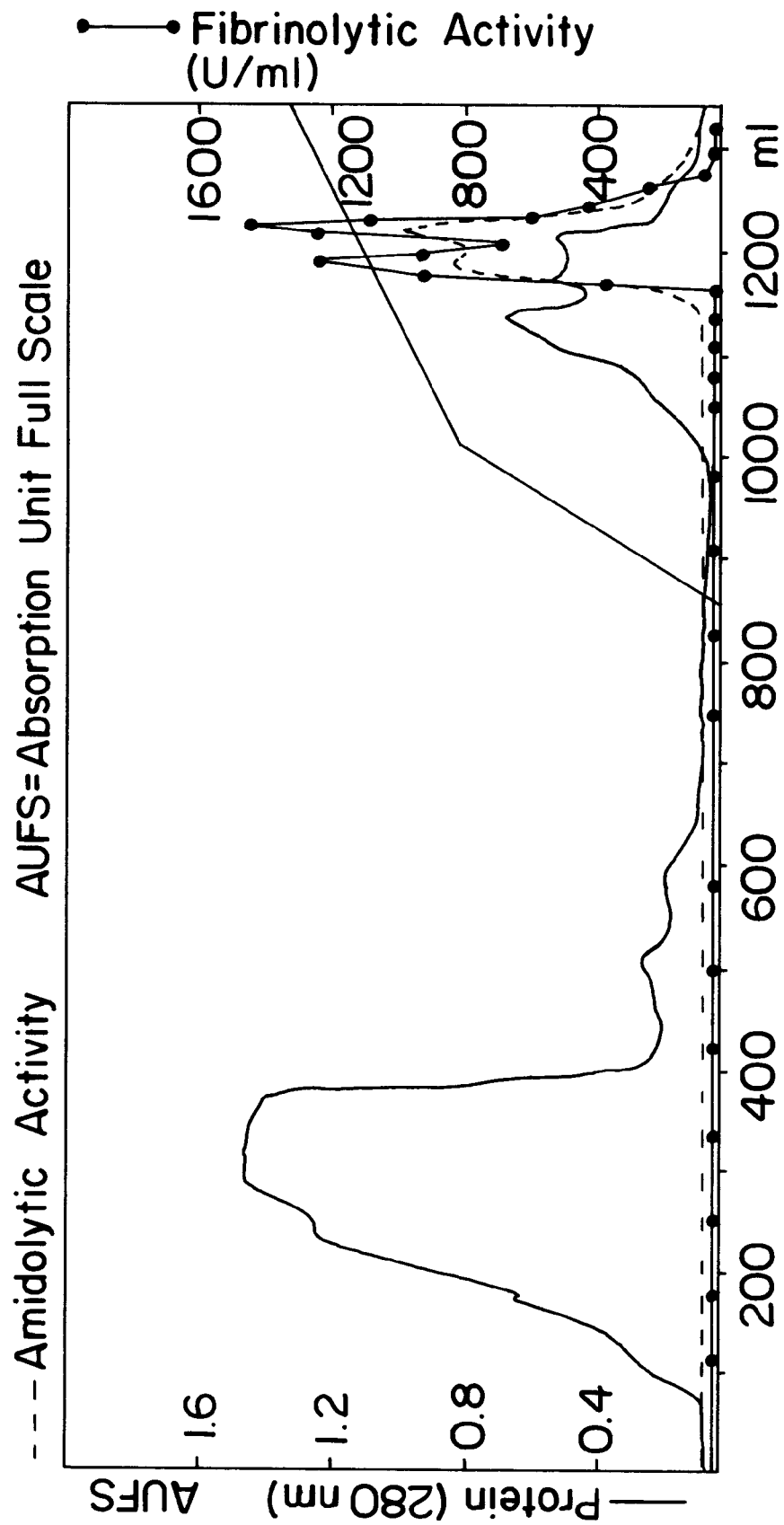
FIG. 1 represents a chromatogram of v-PA eluted from a $Zn^{++}$ chelate Sepharose column with imidazole.

Processing of a 60 ml Batch of Saliva from the Vampire Bat *Desmodus rotundus* Containing Primarily Molecular Form v-PA $\beta$ (a) $Zn^{++}$ Chelate "Sepharose" Chromatography 60 ml of saliva is centrifuged at 4° C. and at 6,000 g. This supernatant is set at 20 millimoles Tris pH 7.5/100 mM NaCl/0.01% "Pluronic" F 68 and introduced to a chromatographing column filled with 200 ml of Chelate "Sepharose" fast flow and equilibrated with 10 mM Tris pH 7.5/100 mM NaCl/1 mM imidazole/0.01% "Pluronic" F 68. The column is washed with this buffer until the optical density, measured at 280 nm, has reached the baseline (about 600 ml). Thereafter, the v-PA is eluted with a gradient of 1–50 mM imidazole (1,000 ml) in 10 mM Tris pH 7.5/100 mM NaCl/0.01% "Pluronic" F 68 (FIG. 1). This purifying step is performed at 4° C.

Figure 2:
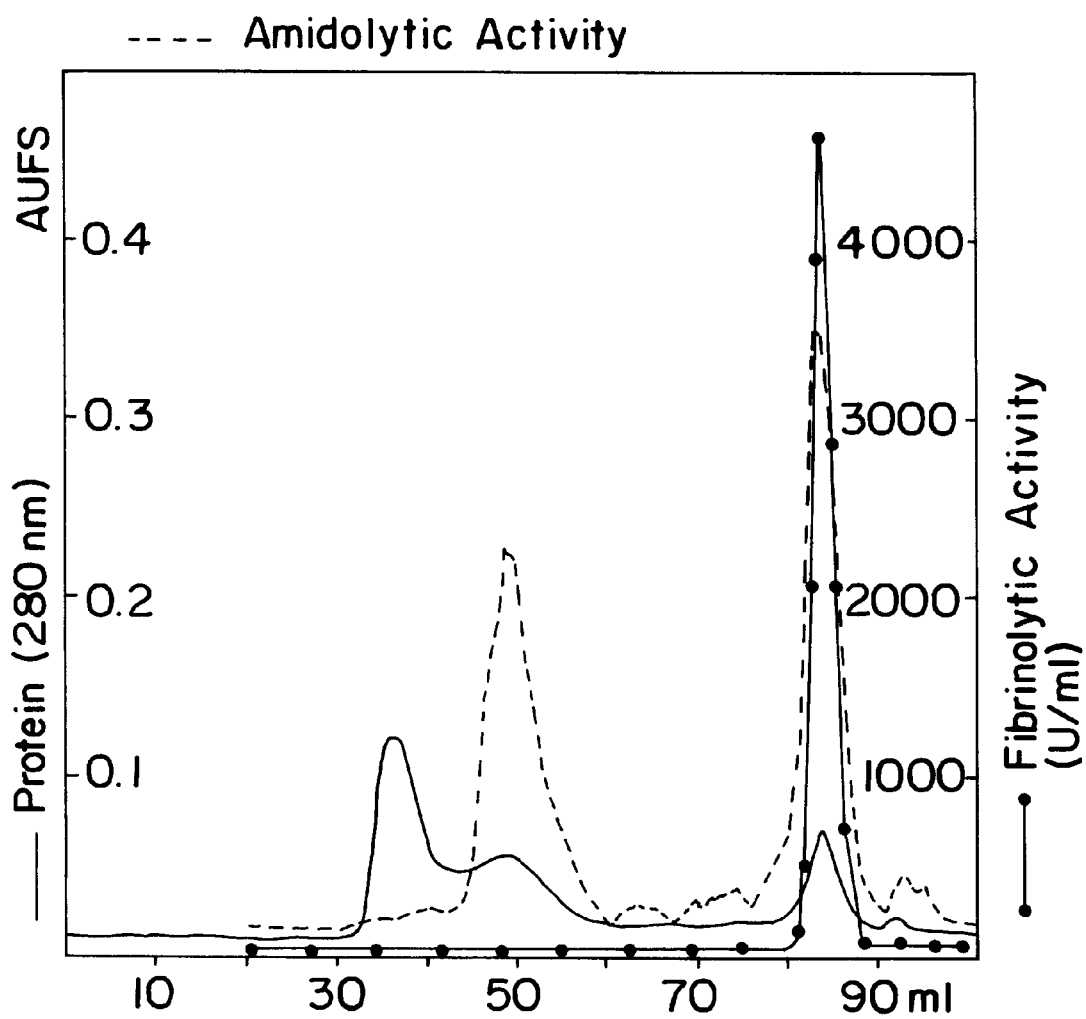
FIG. 2 represents a chromatogram of v-PA pooled from $Zn^{++}$ chelate chromatography eluted from Superose column in the absence of NaCl.

(b) Gel Filtration without NaCl 5 ml of a v-PA-containing fraction from $Zn^{++}$ chelate "Sepharose" chromatography is chromatographed over a "Superose" 12 HR16/50 chromatographing column (Pharmacia) in 20 mM Tris pH 8.0/0.01% "Pluronic" F 68 with the aid of an FPLC system (Pharmacia) (FIG. 2).

With this purification step, a protease is separated having no fibrinolytic activity whatever. The fractions with v-PA activity are pooled.

Figure 3:
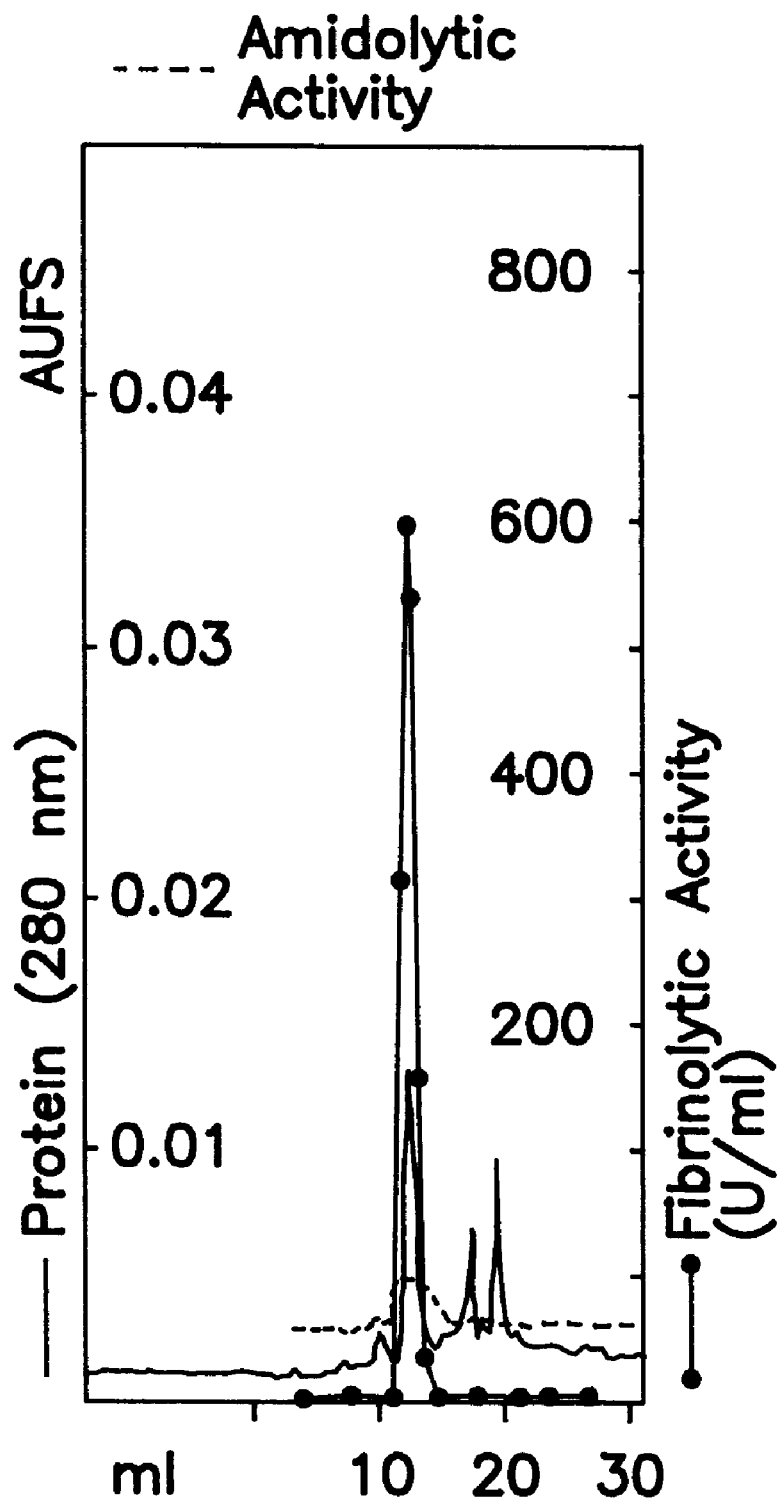
FIG. 3 represents a chromatogram of v-PA pooled from Superose chromatography in the absence of NaCl eluted from Superose column in the presence of 160 mM NaCl.

(c) Gel Filtration with NaCl 2 ml of the above-described v-PA pool is concentrated by freeze-drying to 0.2 ml and chromatographed in 50 mM Tris pH 8.0/160 mM NaCl/0.01% "Pluronic" F 68 over a "Superose" 12 HR 10/30 chromatographing column (Pharmacia) with the aid of an FPLC system (Pharmacia) (FIG. 3).

v-PA is eluted as a homogeneous, sharp peak with a molecular weight of about 40,000.

The result of the purification process is not shown.

Nonreducing SDS polyacrylamide gel electrophoresis was conducted with the sensitive silver staining method, on a sample from each purifying stage. The gel showed that v-PA $\beta$ consists of a protein chain, because during cleaving of the disulfide bridges by DTT, the molecule is not split into two protein bands. Only an apparent rise in molecular weight occurs which can be explained by the linearization of the protein chain by DTT.

Concentrates of the enriched activity are subjected to SDS gel electrophoresis under non-reducing conditions in an 8–25% strength gradient gel. Several of the gels are stained in silver to visualize their proteins; others are washed in "Triton" X-100 (1%) to remove the SDS and placed on a fibrin indicator gel which contains plasminogen (Fibrin-Zymographie; Granelli-Piperno A. and Reich E., J. Exp. Med. 148 : 223–234, 1978).

The activity of the active agent v-PA β, recognizable by a lysis halo in the indicator gel, corresponds to a protein band with an apparent molecular weight of 39,000±3,000. The lysis halo can be detected exclusively on plasminogen-containing fibrin indicator gels, but not on plasmogen-free fibrin indicator gels or on plasminogen-containing casein indicator gels. t-PA, subjected to an identical process, produces lysis halos also in plasminogen-containing casein indicator gels.

The activity of the purified active agent v-PA β is thus identical to a protein with an apparent molecular weight of 43,000±2,000 (under reducing conditions in SDS polyacrylamide electrophoresis) converting plasminogen into plasmin in the presence of fibrin, leading to the dissolution of the fibrous substance fibrin. In contrast to t-PA which can activate plasminogen also in the presence of casein, v-PA β is incapable of converting plasminogen into plasmin in the presence of casein.

The present invention can be furthermore characterized on the basis of the examples set out below:

Example 2
Purification and Separation of v-PA $\alpha_1$ and v-PA β from the Saliva of the Vampire Bat *Desmodus rotundus*

Figure 4:
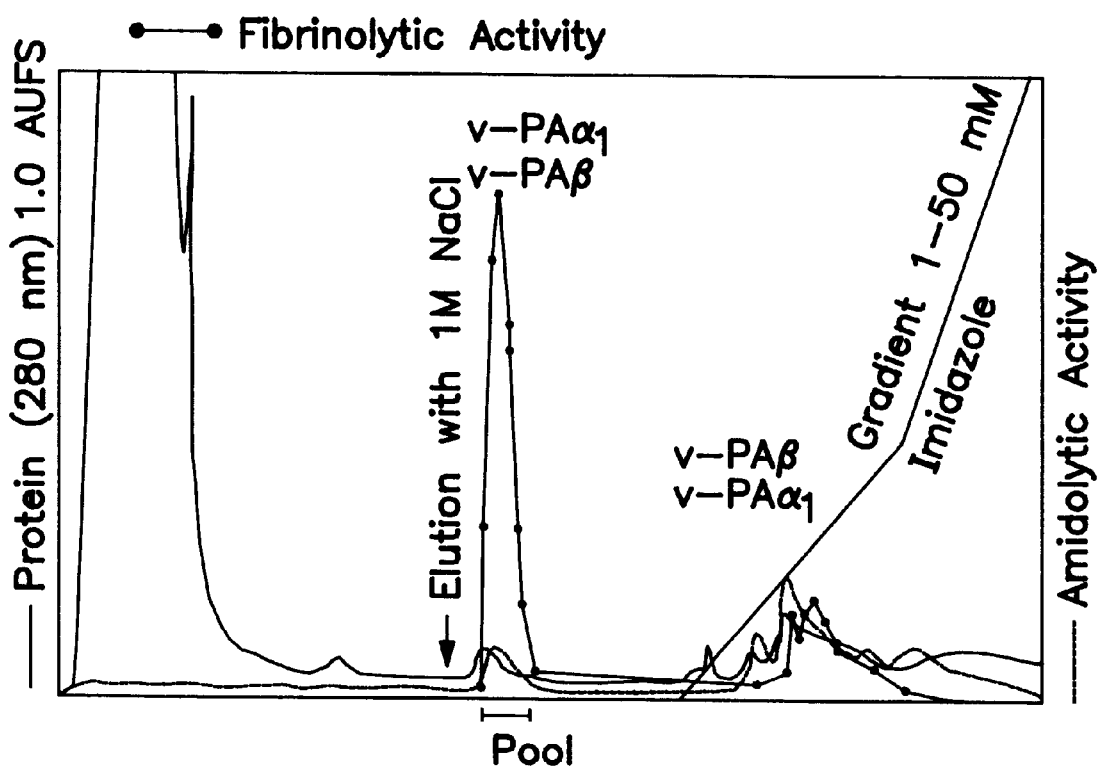
FIG. 4 represents a chromatogram of v-PA $\alpha_1$ and v-PA $\beta$ eluted from a $Zn^{++}$ chelate Sepharose column.

(a) $Zn^{++}$ Chelate "Sepharose" Chromatography 20 ml of saliva is centrifuged at 4° C. and 6,000 g. The supernatant is adjusted to 20 mM Tris pH 7.5/100 mM NaCl and 0.05% "Pluronic" F 68. A chromatographing tube is filled with 8 ml of $Zn^{++}$ chelate "Sepharose" equilibrated with 10 mM Tris pH 7.5/100 mM NaCl/1 mM imidazole/0.05% "Pluronic" F 68, and the saliva supernatant is chromatographed thereover. The column is washed with equilibrating buffer. Thereafter, with 10 mM Tris pH 7.5/1 M NaCl/1 mM imidazole/0.05% "Pluronic" F 68, primarily v-PA $\alpha_1$ is eluted, which still contains a small proportion of v-PA β (FIG. 4). Then, v-PA β, still containing a small proportion of v-PA $\alpha_1$, is eluted with a gradient of 1–50 mM imidazole in 10 mM Tris pH 7.5/100 mM NaCl/0.05% "Pluronic" F 68.

(b) Hydroxyapatite Chromatography

Figure 5:
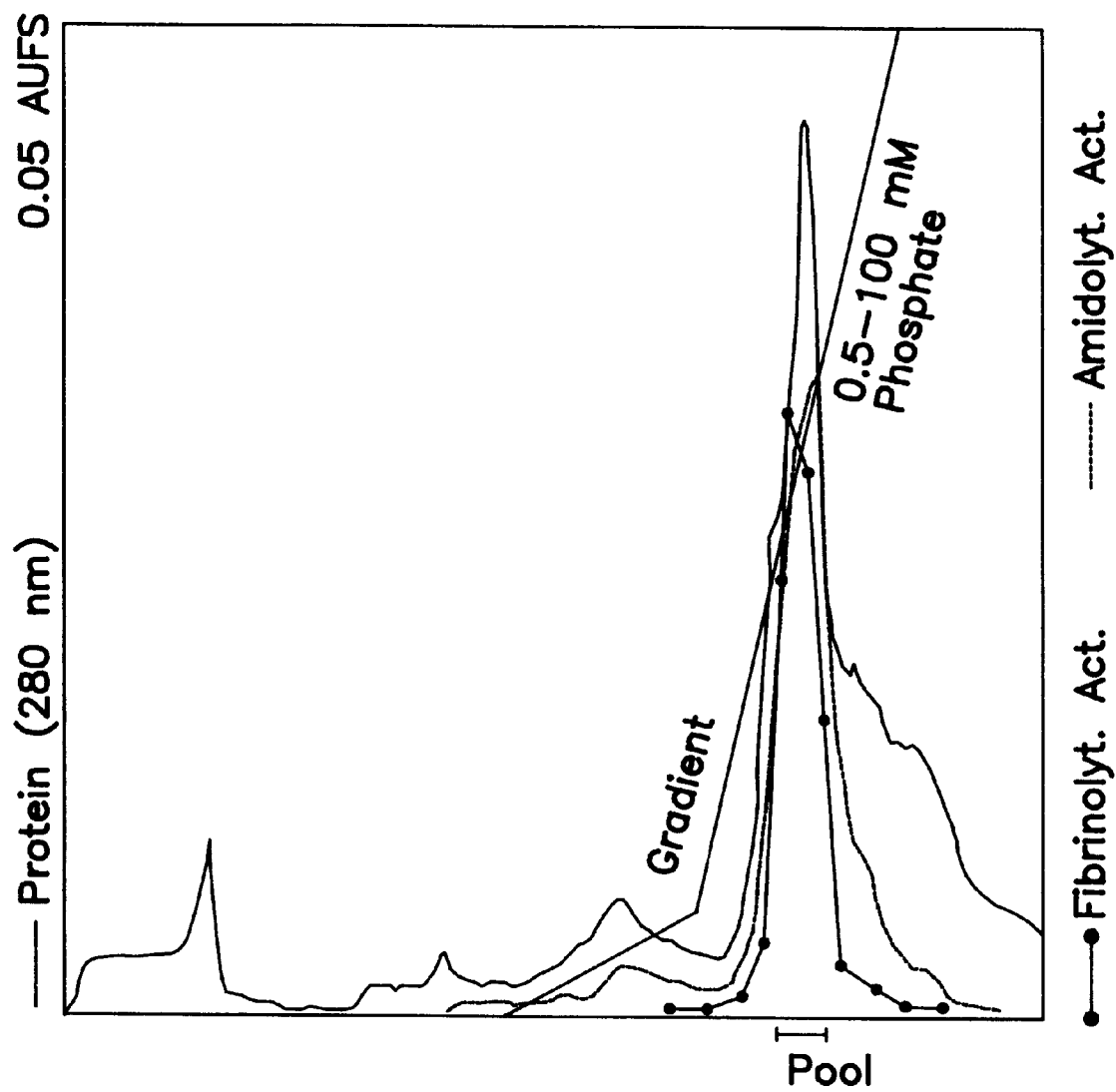
FIG. 5 represents a hydroxyapatite chromatography of pool from $Zn^{++}$ chelate chromatography.

A chromatographing column is charged with 8 ml of hydroxyapatite and equilibrated with 50 mM Tris pH 8.0/500 mM NaCl/0.01% "Pluronic" F 68. The pool from $Zn^{++}$ chelate chromatography (FIG. 4) is passed over the hydroxyapatite column and washed with the equilibrating buffer, and the v-PA is eluted with a gradient of 0.5–100 mM Na phosphate pH 7.5 in 500 mM NaCl/0.01% "Pluronic" F 68 (FIG. 5). The active fractions are pooled.

(c) Gel Filtration

Figure 6:
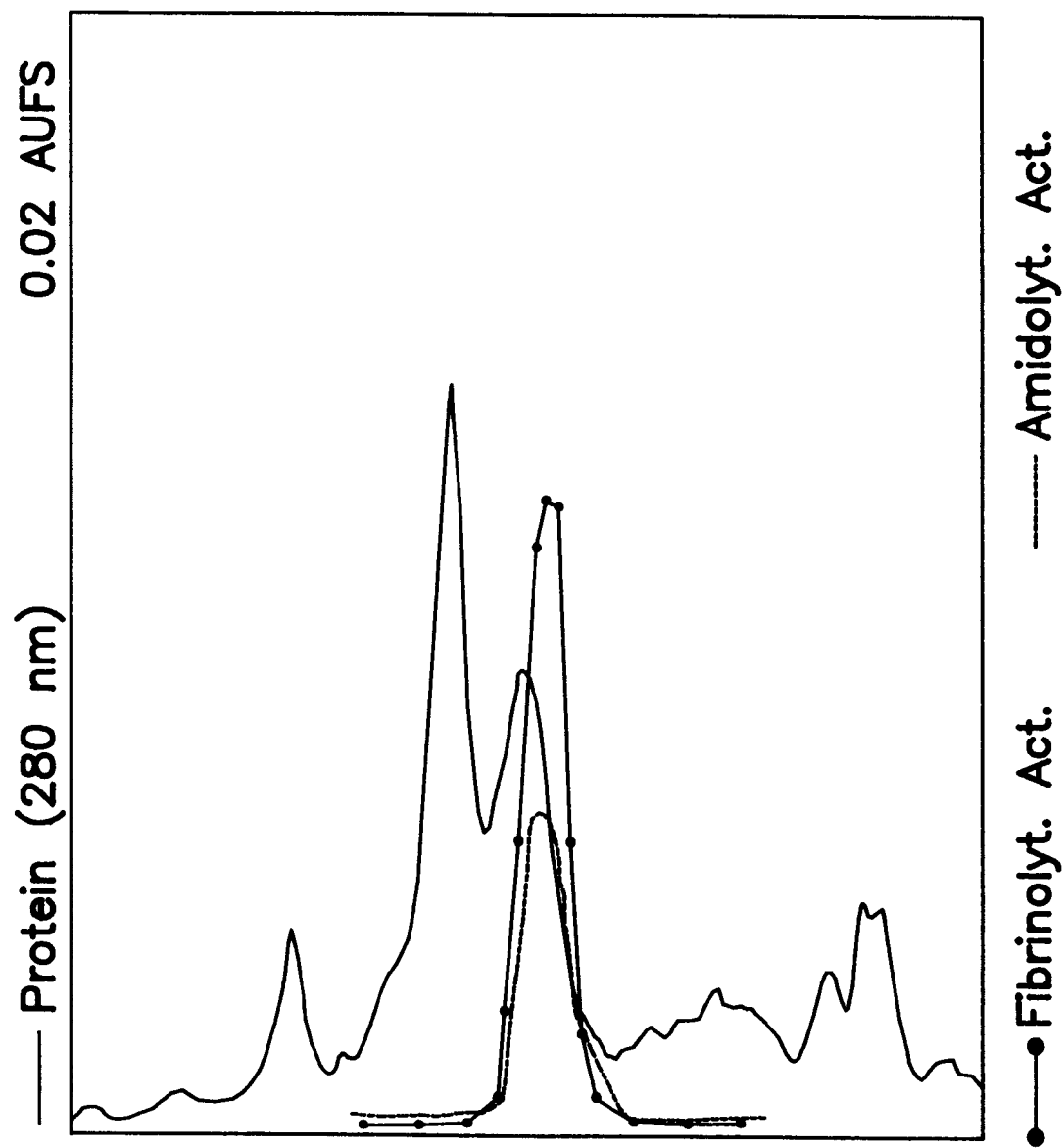
FIG. 6 represents a gel filtration of pool from hydroxyapatite chromatography.

The pool from the hydroxyapatite chromatography (FIG. 5) is dialyzed against 20 mM Tris pH 8.0/160 mM NaCl and concentrated to 0.6 ml by freeze-drying. This concentrate is filtered with the aid of an FPLC system (Pharmacia) over a "Superose" 12 HR 16/50 column (FIG. 6).

When analyzing a concentrate of the active fractions of the gel filtration with the aid of SDS polyacrylamide gel electrophoresis under non-reducing conditions, and thereafter staining the gel with "Coomassie" blue, a protein band becomes visible having a molecular weight of 43,000 (not shown).

As could be seen from that gel, v-PA $\alpha_1$ is free of other proteins. Also this purified v-PA $\alpha_1$ yields, as described in Example 1c, a lysis halo with an identical molecular weight of 43,000 in an indicator gel (fibrin zymography). Also, this lysis halo can be found exclusively on a plasminogen-containing fibrin indictor gel, and not on a plasminogen-containing casein indicator gel.

Example 3
Binding and Elution of v-PA $\alpha_1$ and v-PA β to the Trypsin Inhibitor DE-3 from the Seeds of *Erythrina latissima* (ETI)

50 mg of ETI (Erytech Services LTD, Arcadia, South Africa) is coupled in covalent fashion to 6.6 g of activated CH "Sepharose" 4B (Pharmacia) in accordance with the manufacturer's data. With 1 M Tris pH 6.8, 16 ml of saliva is adjusted to pH 7.5 and centrifuged for 10 minutes at 4° C. and 6,000 g. A chromatographing tube HR 10/2 (Pharmacia) is filled with 2 ml of ETI CH "Sepharose" 4 B (see above). With the aid of an FPLC system (Pharmacia), this affinity chromatography is conducted. For this purpose, the saliva supernatant is passed over the ETI CH "Sepharose" 4B and thoroughly washed with 20 mM Tris pH 7.5/400 mM NaCl/0.01% "Pluronic". Elution is performed with a solution of 20 mM Tris pH 7.5/400 mM NaCl/1.6 M KSCN/0.01% "Pluronic" F 68. During this step, the fibrinolytic as well as the amidolytic activity is eluted together with one protein peak.

When analyzing this chromatography with the aid of SDS polyacrylamide gel electrophoresis under nonreducing conditions, a strong enrichment of the two v-PA forms v-PA $\alpha_1$ and v-PA β can be confirmed.

The two molecular v-PA forms occurring in this batch of saliva bind, under the above-mentioned conditions, to ETI-CH "Sepharose" 4B and can be eluted in the presence of 1.6 M KSCN or other chaotropic compounds. This holds true for all forms of the active agent.

Example 4
Binding and Elution of Active Agents v-PA $\alpha_1$ and v-PA β to Heparin "Sepharose"

Figure 7:
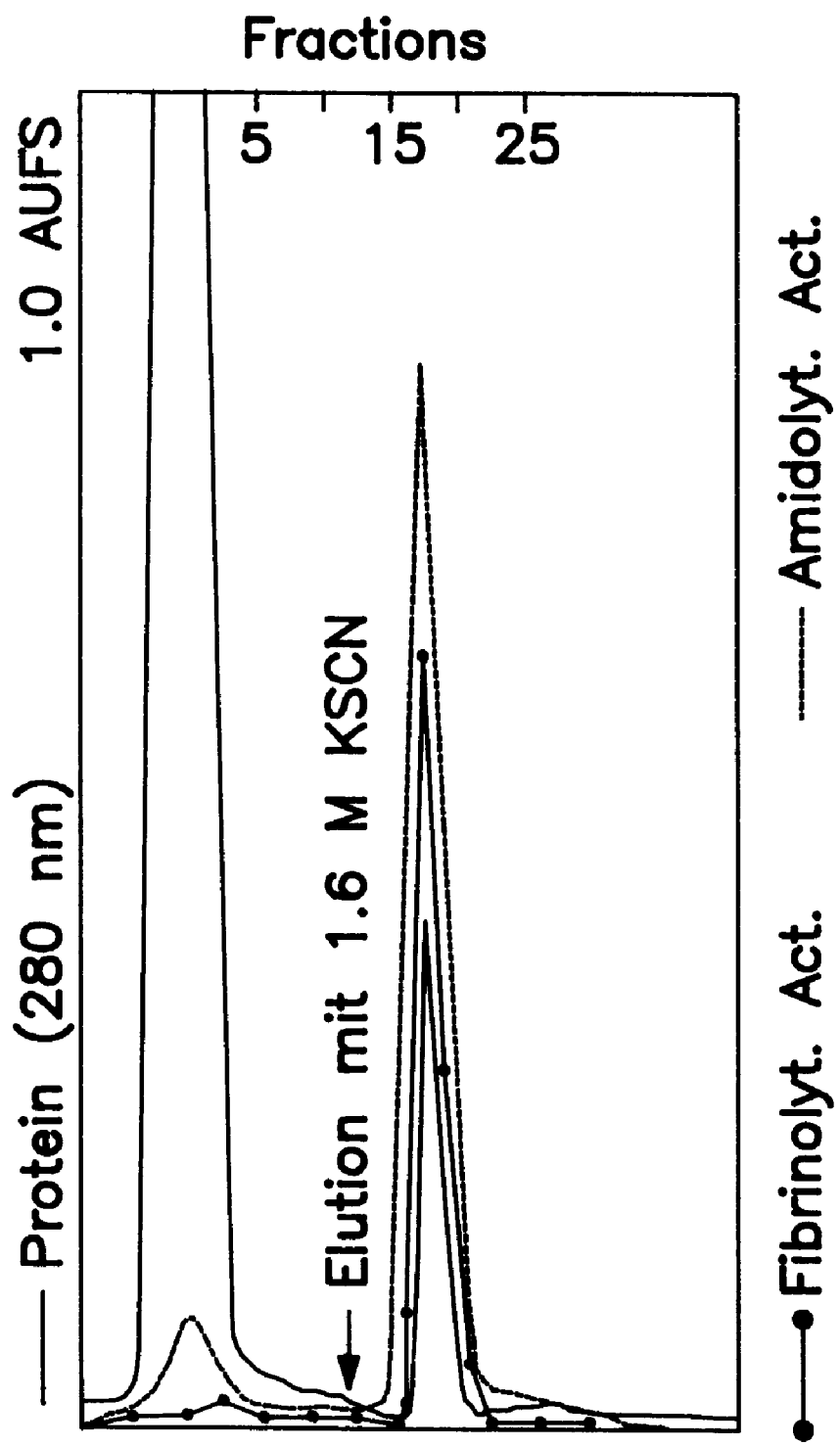
FIG. 7 represents an ETI Sepharose 4B chromatography of bat saliva.
Figure 8:
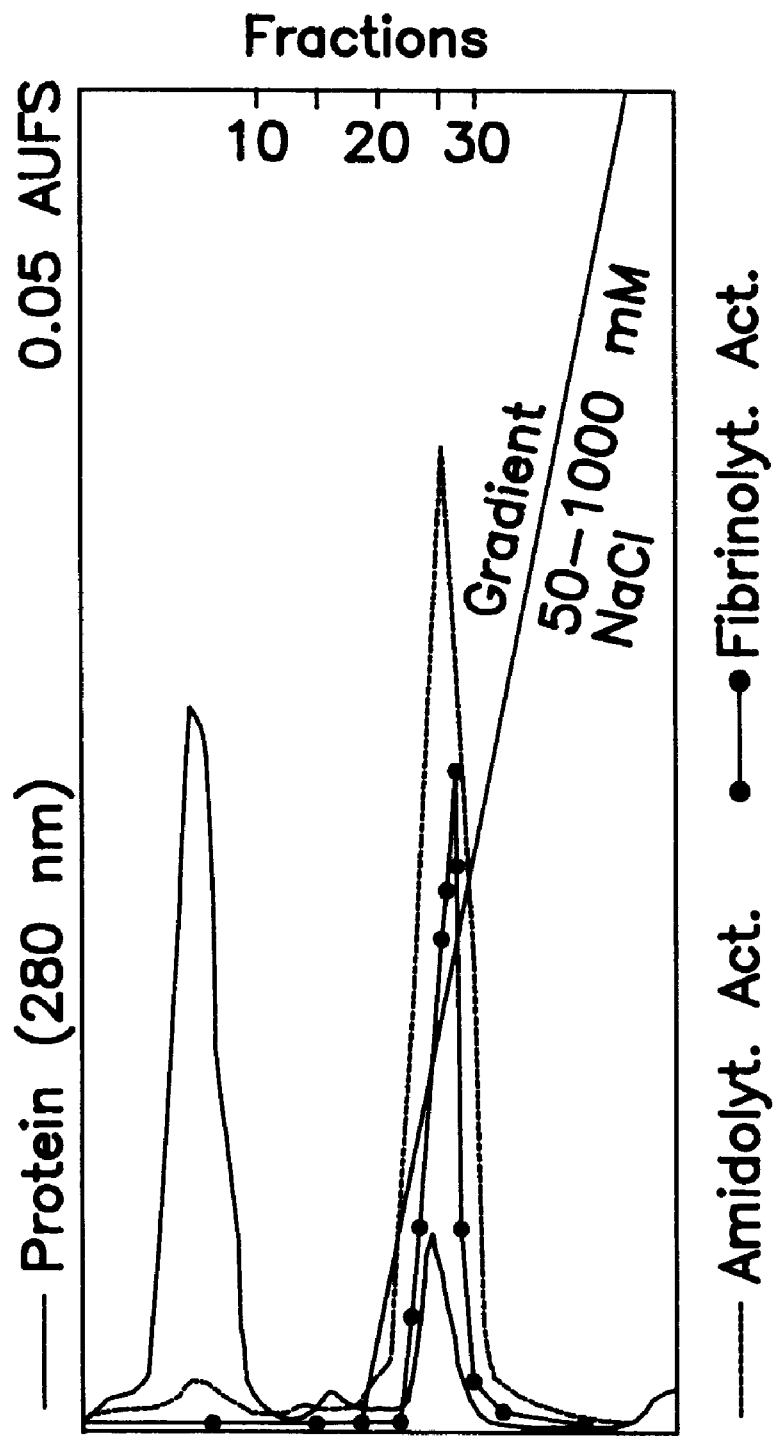
FIG. 8 represents a heparin Sepharose chromatography of v-PA active agent prepurified from ETI-CH Sepharose 4B (Example 3, FIG. 7)

An unpacked FPLC column (HR 5/5) is filled with one milliliter of heparin "Sepharose" (Pharmacia). Fraction 18 from ETI-CH "Sepharose" 4B chromatography (Example 3, FIG. 7) is dialyzed against 20 mM Tris pH 7.5/50 mM NaCl/0.01% "Pluronic" F 68 and chromatographed over heparin "Sepharose" with the aid of an FPLC system (Pharmacia). After application of the dialyzate, the column is washed with 20 mM Tris pH 7.2/50 mM NaCl/0.01% "Pluronic" F 68, and then eluted with a gradient of 50–1,000 mM NaCl in 20 mM Tris pH 7.2/0.01% "Pluronic" F 68 (FIG. 8).

With the aid of heparin "Sepharose" chromatography, it is possible, for example, to bind and elute the molecular forms v-PA $\alpha_1$ and v-PA β, i.e. to purify them. As can be seen from FIG. 8, the molecular v-PA form, v-PA β, shows a weaker binding to heparin "Sepharose" than the molecular v-PA $\alpha_1$ form; i.e. for the elution of v-PA β, a lower NaCl concentration is adequate than is needed for elution of v-PA $\alpha_1$. Thus, with the aid of the chromatographical methods disclosed in this example, it is possible to separate the two v-PA forms from each other.

Example 5
Binding and Elution of Active Agents v-PA $\alpha_1$ and v-PA β to Fibrin "Celite"

Figure 9:
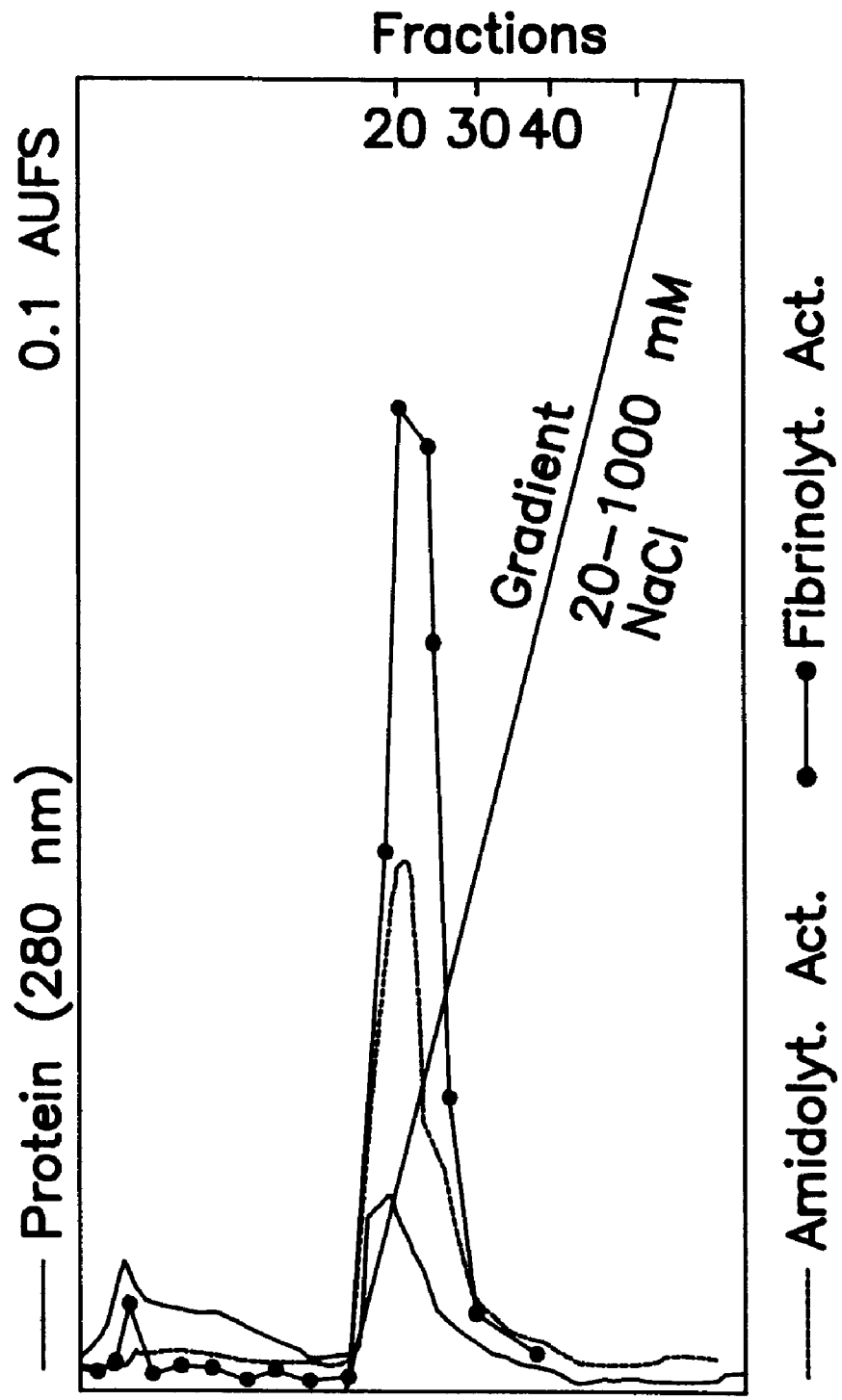
FIG. 9 represents a fibrin Celite chromatography of v-PA active agent (v-PA $\alpha_1$ and v-PA $\beta$) prepurified on ETI-CH Sepharose 4B (Example 3, FIG. 7)

The affinity medium fibrin "Celite" is prepared according to known directions (Husain, S., Lipinski, B. and Gurewich, V. in Proc. Nati. Acad. Sci. USA 78 : 4265–4269, 1981). One milliliter of the fibrin "Celite" material is filled into a chromatographing column HR 5/5 (Pharmacia). Fraction 17 from ETI-CH "Sepharose" 4B chromatography (Example 3, FIG. 7) is dialyzed against 20 mM Tris pH 8.0/20 mM NaCl/0.01% "Pluronic" F 68, and chromatographed over fibrin "Celite" with the aid of an FPLC system (Pharmacia). After application of the dialyzed fraction, washing is performed with 20 mM Tris pH 8.0/20 mM NaCl/0.01% "Pluronic" F 68, and the thus-found active agent is eluted with a gradient of 20–1,000 mM NaCl in 20 mM Tris pH 8.0/0.01% "Pluronic" F 68 (FIG. 9).

The v-PA-containing fractions are subjected to SDS polyacrylamide gel electrophoresis (not shown).

The active agents v-PA $\alpha_1$ and v-PA $\beta$ bind, at low NaCl concentrations, to fibrin "Celites" and can be again eluted by increasing the NaCl concentration in the buffer. During this step, one can observe that v-PA $\beta$ obviously shows weaker binding to fibrin "Celites" than v-PA $\alpha_1$ since, in contrast to v-PA $\beta$, the v-PA $\alpha_1$ form elutes only at higher NaCl concentrations. Thus, this purifying method can also be utilized for separation of v-PA $\beta$ and v-PA $\alpha_1$.

Example 6
N-Terminal Amino Acid Sequence Analysis of the Purified v-PA Forms v-PA $\alpha_1$ and v-PA $\beta$ Fractions containing purified v-PA $\alpha_1$ (Example 2) or purified v-PA $\beta$ (Example 1) are subjected, after dialysis against a suitable buffer, to a 12.5% polyacrylamide gel electrophoresis under nonreducing conditions. After electrophoresis has taken place, the gel is removed from the electrophoretic apparatus and transferred according to a conventional method (Matsudaira, P. in J. Biol. Chem. 262 : 10035–10038, 1987) to a polyvinylidene difluoride membrane (Immobilon, Millipore Corp. USA). The corresponding protein band is excised with a scalpel and, in an automatic 477 A Protein Sequencer/120 A Analyzer (Applied Biosystems USA), the N-terminal amino acid sequence is directly determined. The analyses are repeatedly performed. The sequences set out below are found:

```
v-PA α₁:
1             5              10             15
Ala Tyr Gly Val Ala X Lys X Glu Ile Thr Gln Met Thr Tyr Arg v-PA β:
1             5              10             15
Ala Tyr Gly Gly X Ser Glu Leu Arg Cys Phe Asn Gly Gly Thr X Gln Ala Ala (X = not clearly determined)
```

With the aid of these thus-determined sequences, a cDNA bank was screened from the saliva gland of *Desmodus rotundus* (Example 18).

Example 7
Comparison of Plasminogen Activation of Active Agent v-PA $\beta$, Purified According to Example 1, with t-PA By incubating a specific plasminogen activator (PA) with an adequately high concentration of plasminogen (PLG) in a buffer environment, e.g. 50 mM Tris pH 7.4, 20 mM NaCl at 37° C., then plasmin is produced according to the following principle:

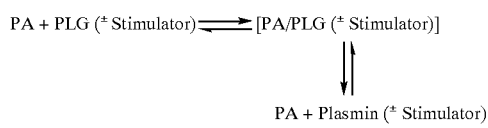

The thus-formed plasmin can be detected by a chromogenic tripeptide H-D-Val-Leu-Lys-pNA (S 2251) extensively specific for this protease. This reaction proceeds according to the following principle:

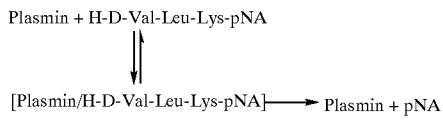

Figure 10:
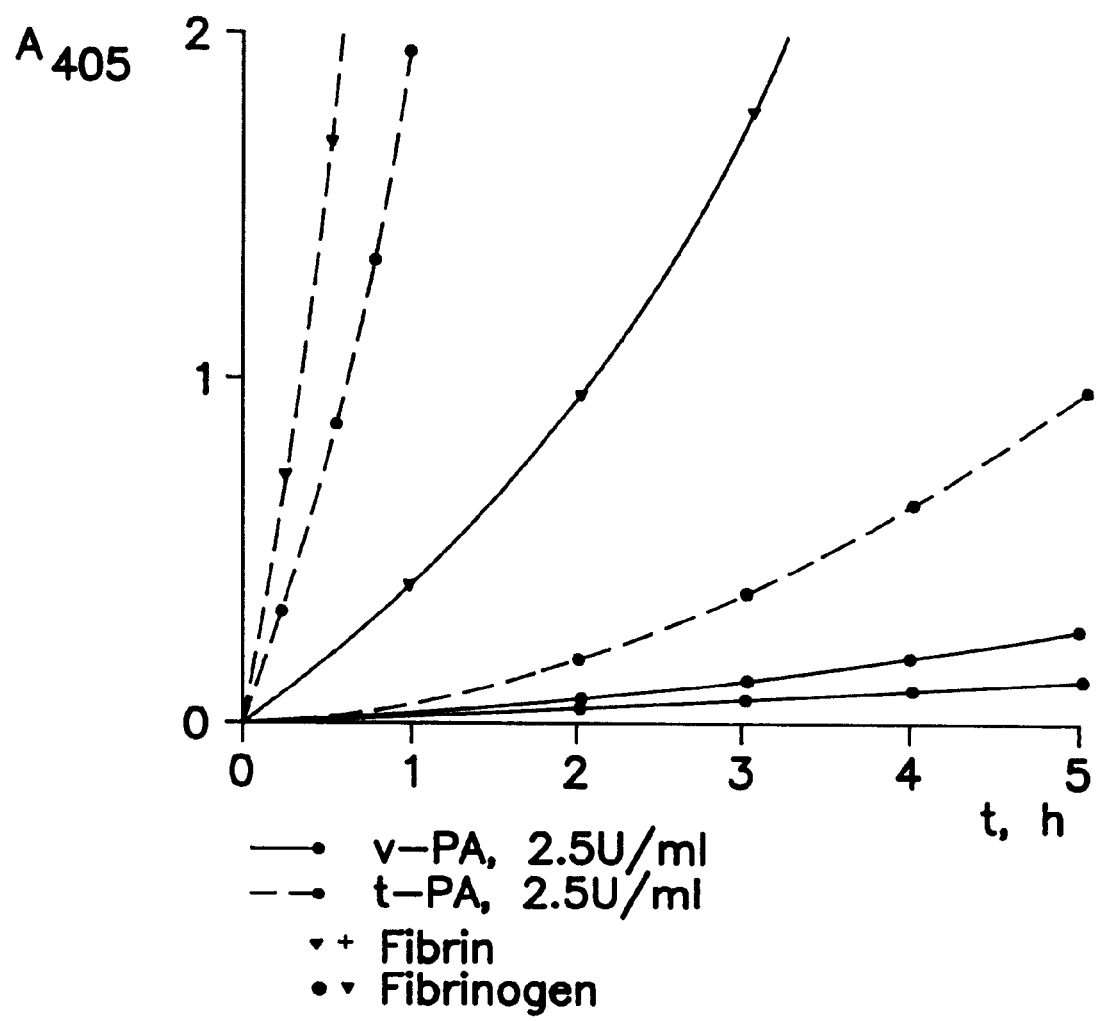
FIG. 10 represents a plasmin production rate of v-PA $\beta$ as compared with t-PA in the presence and absence of fibrin or fibrinogen.

The production rate of pNA (p-nitroaniline) can be determined photometrically at 405 nm and is proportional to the concentration of the enzyme plasmin. By coupling the two principles, it is thus possible to measure the formation rate of plasmin, which is an expression of the activity of the plasminogen activator. FIG. 10 shows the plasmin formation rates of t-PA and of v-PA in the absence and in the presence of the stimulators fibrinogen (the clotting substrate) and fibrin (the fibrous substance in the blood clots to be dissolved).

The test is performed on 96-hole microtiter plates. Each hole contains a total volume of 220 µl. The concentration of plasminogen is 0.5 µM; of H-D-Val-Leu-Lys-pNA 0.68 mM; of t-PA 0.05 IU; the utilized activity of v-PA, determined in the International Clot-Lysis Assay (Gaffney, P. J., Curtis, A. D., Thrombos. Haemostas, 53 : 134–136, 1985), is ten times higher, i.e. about 0.5 U. The concentration of the stimulators amounts to about 20 µg/hole.

Accordingly, t-PA also activates plasminogen even in the absence of a stimulant and with a very high activation rate even in the presence of fibrinogen. In the described assay, v-PA activates plasminogen exclusively in the presence of the fibrous substance fibrin.

Example 8
Comparison of Thrombolytic Activity of v-PA $\alpha_1$ and v-PA $\beta$ with That of t-PA The thrombolytic activity of the novel active agent is examined in comparison with t-PA in a newly developed "Micro-Clot-Lysis Assay" (MCLA). Respectively 100 µl of fresh human whole blood is pipetted into the holes of microtiter plates, combined with respectively 10 µl of a clotting agent ("Thromborel", Behring-Werke), and incubated at 37° C. for 1 hour. The resultant blood clots are washed twice with phosphate-buffered sodium chloride solution (PBS) before they are combined with 100 µl of autologous plasma previously obtained by centrifuging. The plasma is subsequently combined with t-PA and, respectively, v-PA in concentrations of 1.56–12.5 U/ml. The thus-treated microtiter plates are stored for 18 hours at 37° C. in a moist chamber. After elapse of the incubating period, the plates are shaken on a vibrating table (Red Rotor), and thereafter a plasma specimen is withdrawn from each hole, diluted with twice-distilled water 1:6 (leads to rupturing of the red blood cells liberated by lysis), and the thus-released red blood pigment is determined photometrically at 492 nm in a microtiter plate photometer.

Figure 11A:
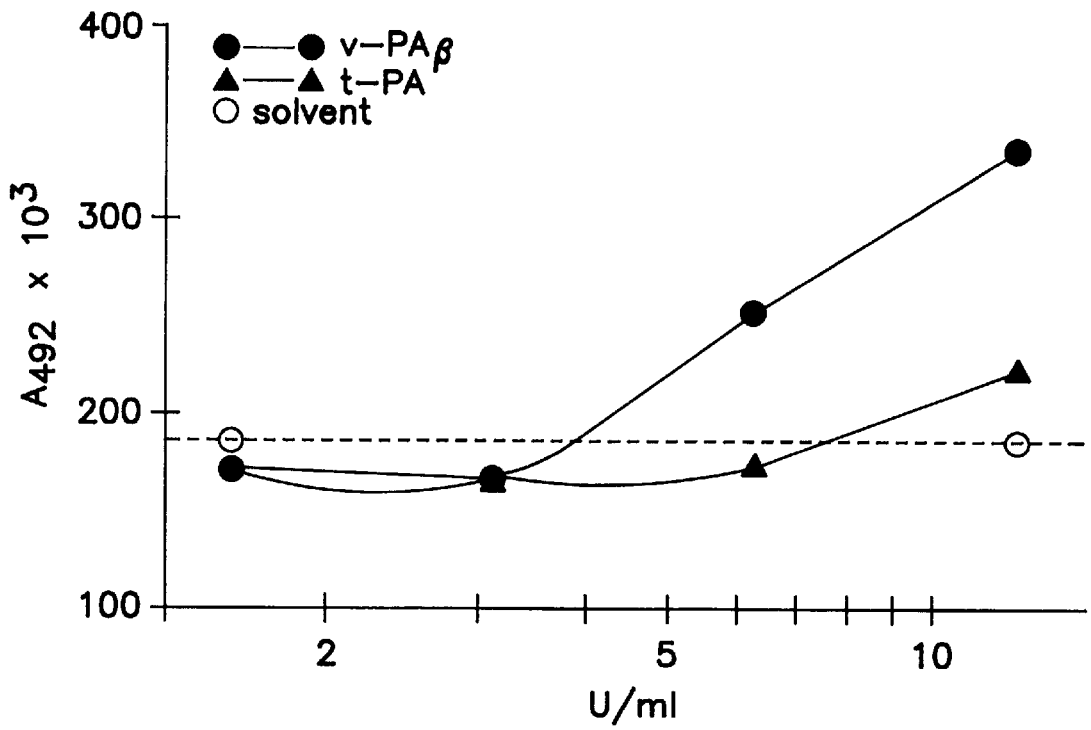
FIG. 11(A) represents a human whole blood clot lysis in vitro comparing the effect of plasminogen activators v-PA $\beta$ and t-PA.
Figure 11B:
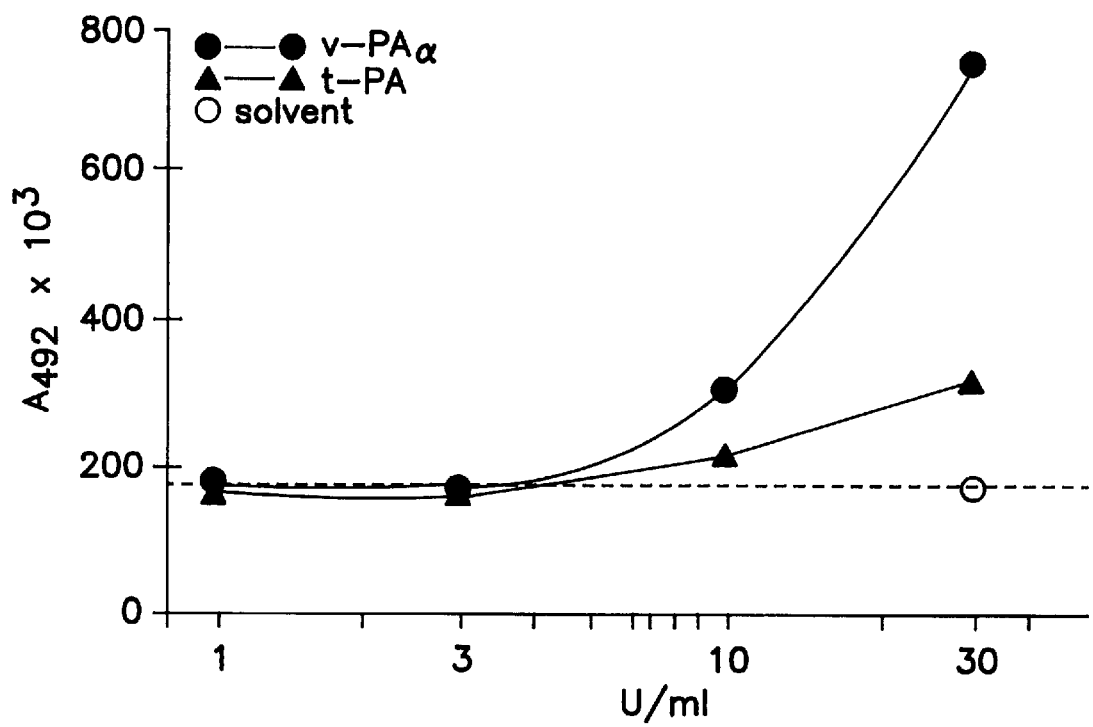
FIG. 11(B) represents a human whole blood clot lysis in vitro comparing the effect of plasminogen activators v-PA $\alpha_1$ and t-PA.

The result of the test can be seen from FIGS. 11A and 11B: In comparison with a standard t-PA, equieffective concentrations of the novel active agent lyse (as determined in the International Clot-Lysis Assay) human whole blood thrombi better than t-PA. Even about 3 U/ml of the novel active agent v-PA β shows, in the described test model, a significant thrombolytic effect whereas 3μ t-PA shows no results deviating from the control.

In a similar experiment, the time dependency of the human whole blood thrombolysis by t-PA and v-PA is investigated.

Figure 12A:
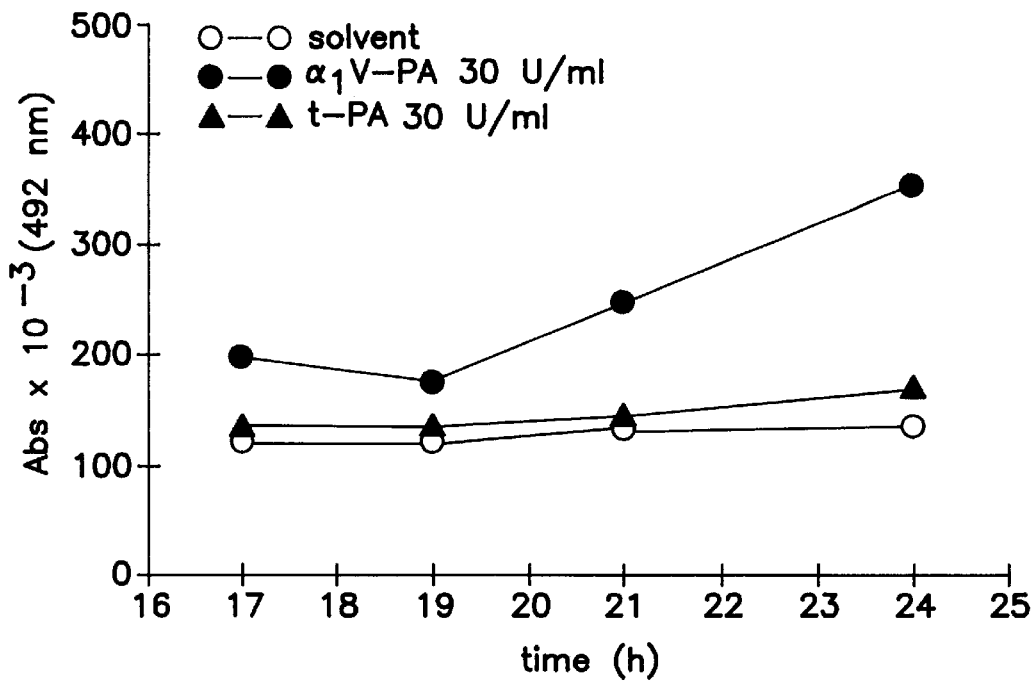
FIG. 12(A) represents a time-dependency of human whole blood clot lysis in vitro comparing t-PA and v-PA $\alpha_1$ at 30 U of each.
Figure 12B:
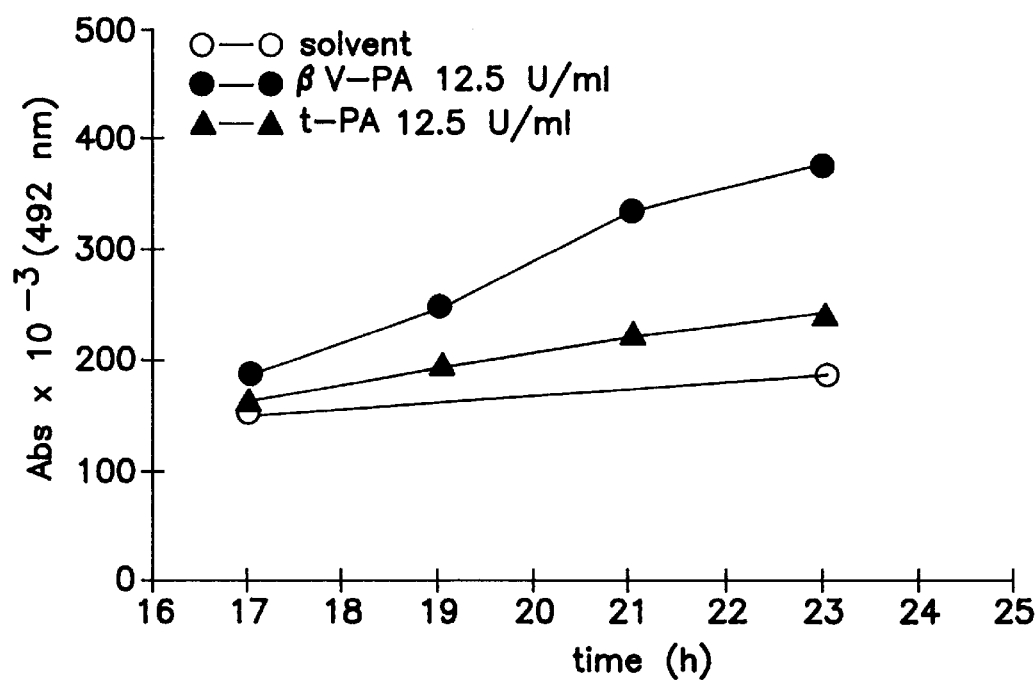
FIG. 12(B) represents a time-dependency of human whole blood clot lysis in vitro comparing t-PA and v-PA $\beta$ at 12.5 U of each.

Respectively 6.25 U and 12.5 U of t-PA and of v-PA are incubated in the above-described system for 23 hours at 37° C. After 15 hours, a sample is withdrawn every 2 hours and prepared as described for the photometric test. The result is illustrated in FIGS. 12A and 12B.

The beginning of thrombolysis, measured as release of red blood cells from the thrombus, is clearly more rapid with the active substance than with t-PA. 6.25 Units of the new active substance reveal an enhanced thrombolysis after 23 hours as the double activity of t-PA (12.5 Units).

Example 9
Serine Proteases React Specifically with the "Active Site Titrant" Diisopropyl Fluorophosphate (DIFP)

For this purpose, the active agent is buffered to pH 8.0 and mixed in a ratio of 1:20 with 3H-DIFP in propylene glycol. The batch is incubated overnight at room temperature. An aliquot of the batch is separated on a 12.5% SDS gel under nonreducing conditions. The gel is then incubated for 30 minutes at room temperature in "Amplify" (Amersham) and subsequently dried. Then the gel is exposed for 4 days and subsequently the X-ray film is developed. Serine proteases which have the radioactively labeled DIFP incorporated therein become visible on the film as blackened bands (not shown). t-PA yields, for example, a slightly blackened main band with the apparent molecular weight of 68,000±5,000; in contrast thereto, the novel active agent shows a strongly blackened main band of 39,000±2,000 molecular weight (v-PA β) and a blackened band at 43,000±2,000 (v-PA $\alpha_1$).

A control gel obtained under identical electrophoretic conditions is washed with 1% "Triton" X-100 and subsequently placed on a fibrin- and plasminogen-containing indicator gel. The position of the activities of the electrophoresed active agent are congruent with the blackened band of the 3H-DIFP labeled serine proteases representing the active principle of the agent.

Example 10
Fibrinogen Degradation in Vitro of t-PA and v-PA β

When incubating t-PA in human plasma at 37° C., the concentration of clottable fibrinogen decreases in dependence on time. This is due to the relative fibrin specificity of t-PA and is a characteristic property of this thrombolytic. A solution is prepared from 3 mg of clottable human fibrinogen and respectively 1 ml of 50 mM Tris pH 7.4, 40 mM NaCl, and the solution is combined with 1 μM of human plasminogen. A portion of the aliquot batch is combined with 3.1; 6.25; and 12.5 U of t-PA and, respectively, with the same activities of v-PA. A third batch without plasminogen activator serves as the control. Respectively 6 batches are utilized per treatment group. Immediately upon addition of the plasminogen activators, respectively one aliquot is removed from all batches, and the clottable fibrinogen is determined by using the method according to Clauss (Clauss, V. A., Acta Haematol. 17 : 237–246, 1957). A portion of the aliquot is furthermore analyzed by gel electrophoresis. Further withdrawals of aliquots from the batches incubated at 37° C. are made after 2, 4, and 6 hours. The results of the fibrinogen measurements can be seen from Table 1.

TABLE 1

| Incubation Period/h | U/ml 12.5 | t-PA 6.25 | 3.1 | v-PA 12.5 | 6.25 | 3.1 | K + Plg |
|---|---|---|---|---|---|---|---|
| 0 | 10.3 | 9.1 | 9.1 | 10.5 | 10.3 | 10.1 | 10.0 [sec] |
|  | 10.0 | 9.1 | 10.6 | 10.4 | 9.1 | 10.4 | 9.7 |
|  | 10.2 | 9.4 | 9.9 | 10.5 | 10.0 | 10.3 | 9.9 |
|  | 12.6 | 11.3 | 10.5 | 10.0 | 9.7 | 8.9 | 9.5 |
|  | 12.8 | 11.0 | 10.8 | 9.4 | 9.6 | 9.8 | 9.7 |
|  | 12.7 | 11.2 | 10.1 | 9.7 | 9.7 | 9.4 | 9.6 |
| 2 |  |  |  | 12.8 | 11.9 | 11.6 | 10.9 |
|  |  |  |  | 12.5 | 11.2 | 11.5 | 11.1 |
|  |  |  |  | 12.7 | 11.6 | 11.6 | 11.0 |
|  |  | >300 |  | 11.3 | 11.5 | 10.5 | 12.1 |
|  |  |  |  | 11.4 | 11.2 | 10.6 | 11.9 |
|  |  |  |  | 11.4 | 11.4 | 10.6 | 12.0 |
|  |  |  |  | 11.4 | 11.4 | 10.6 | 12.0 |
| 4 |  |  |  | 14.5 | 13.1 | 12.8 | 12.4 |
|  |  |  |  | 13.7 | 13.1 | 11.9 | 12.6 |
|  |  | >300 |  | 14.1 | 13.1 | 12.4 | 12.5 |
|  |  |  |  | 18.6 | 11.6 | 13.2 | 11.8 |
|  |  |  |  |  | 12.1 | 14.2 | 12.4 |
|  |  |  |  |  | 11.9 | 13.7 | 12.1 |
| 6 |  |  |  | 13.9 14.4 | 17.6 | 12.2 13.1 | 12.6 |
|  |  |  |  | 13.1 13.6 | 17.1 | 15.8 12.3 | 11.8 |
|  |  | >300 |  | 13.8 | 17.1 | 13.4 | 12.2 |
|  |  |  |  | 12.3 | 12.8 | 11.9 | 13.0 |
|  |  |  |  | 12.1 |  | 12.2 | 13.3 |
|  |  |  |  | 12.2 | 121.0 | 12.1 | 13.2 |

Plg = 1 μM Plasminogen 40 μl/ml Batch [50 U/ml] mg Clottable Fibrinogen/ml Batch in 50 mM Tris 40 mM NaCl pH 7.4

The clotting times according to Clauss are set forth in seconds. As early as after two hours of incubation, none of the t-PA-containing batches shows any clottable fibrinogen; the clotting periods were >300 s. In contrast thereto, there are no signs of fibrinogen degradation either in the control batches or in the batches combined with the novel active agent. This experiment demonstrates the substantially higher, if not even absolute, fibrin specificity of the novel active agent v-PA β as compared with t-PA.

In an analysis of the aliquots performed by gel electrophoresis, it can furthermore be confirmed that the fibrinogen in the batches with the novel active agent cannot be distinguished from the fibrinogen in the control batches, even after 6 hours of incubation, whereas only degraded fibrinogen can be detected in the batches with t-PA after a period of merely 2 hours.

Example 11
Fibrin Binding of Various Plasminogen Activators and v-PA $\alpha_1$ and v-PA β

Figure 13:
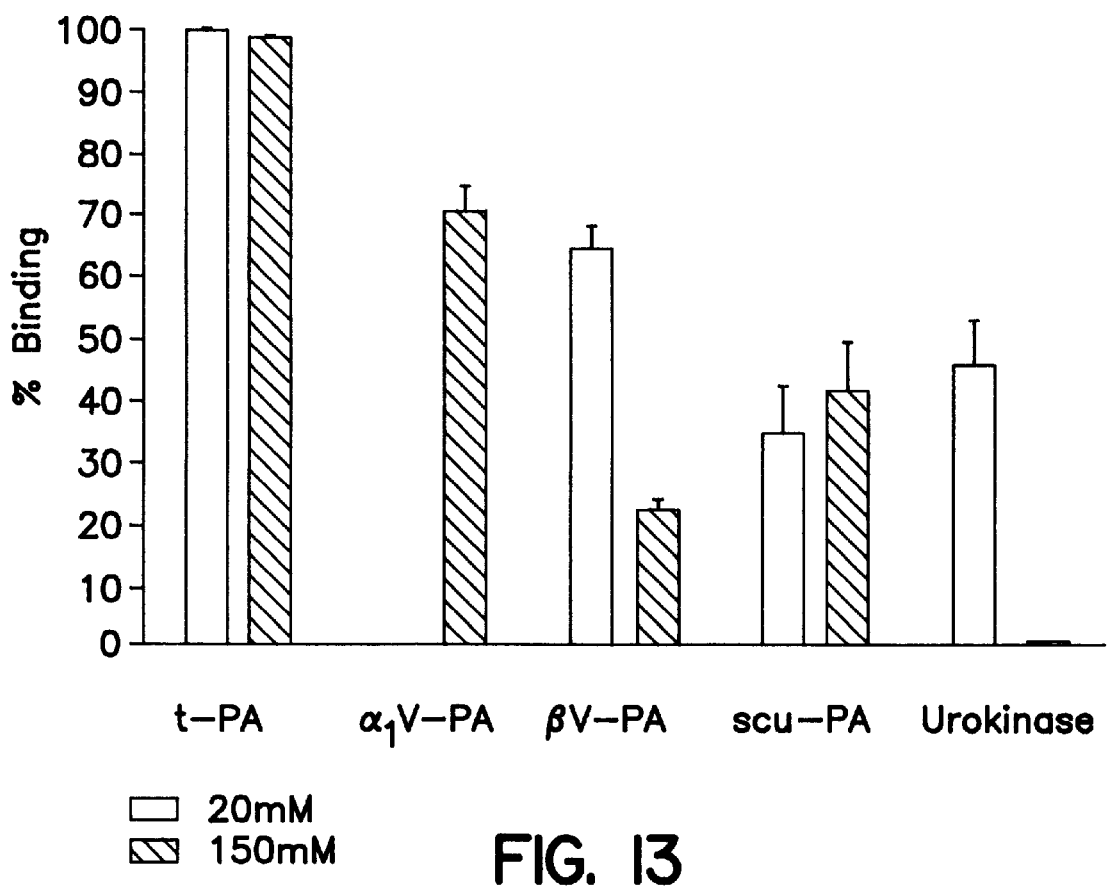
FIG. 13 represents a binding of various plaminogen activators to plamsinogen-free fibrin.

In a specimen pan, 100 µl of plasminogen-free fibrinogen (2 mg/ml) in PBS/0.01% "Tween" 80, 10 µl of the corresponding plasminogen activators in various concentrations, and 10 µl of thrombin (0.3 U) are incubated at 37° C. for 10 minutes. Then the thus-formed fibrin is removed by centrifuging for 5 minutes at 10,000 g, and the residual plasminogen activator activity is determined in the supernatant by means of the fibrin plate testing method and brought into relation with the starting volume. In parallel therewith, under the same conditions, plasminogen activator solutions are prepared without fibrin (control; no binding).

v-PA $\alpha_1$ shows a similarly good fibrin binding as t-PA (FIG. 13). In contrast thereto, v-PA β exhibits a substantially weaker fibrin affinity than v-PA $\alpha_1$. This fibrin affinity displayed by v-PA β is furthermore strongly dependent on the NaCl concentration (FIG. 13).

Example 12
Comparative Kinetics of Glu-Plasminogen Activation by t-PA and v-PA β

(A) In a vessel, 20 µl of plasminogen activator, 10 µl of fibrin monomers (60 µg/ml) in 20 mM Tris pH 7.4/600 mM urea, 50 µl plasmin-free plasminogen (variable concentrations of 0–6 µM in the entire reaction batch) are incubated in 20 mM Tris pH 7.4 and 170 µl 20 mM Tris pH 7.4/0.01% "Tween" 80 at 37° C. under agitation.

(B) In additional tubes, respectively 100 µl of the chromogenic, plasmin-specific substrate S 2251 (3 mM) in water and 400 µl 20 Mm Tris pH 7.4/180 mM NaCl are provided at 37° C.

At various points in time, 20 µl is withdrawn from (A) and transferred into a tube (B), incubated for another hour at 37° C., and the reaction is stopped with 300 µl of 1 M citric acid. The plasmin formed in the incubating batch splits off the peptide group of the chromogenic substrate S 2251 with release of p-nitroaniline. This p-nitroaniline is measured photometrically at 405 nm.

Analogously to the above-described scheme, a calibrating curve is prepared with pure plasmin from which the concentration of thus-formed plasmin can be calculated directly.

Figure 14A:
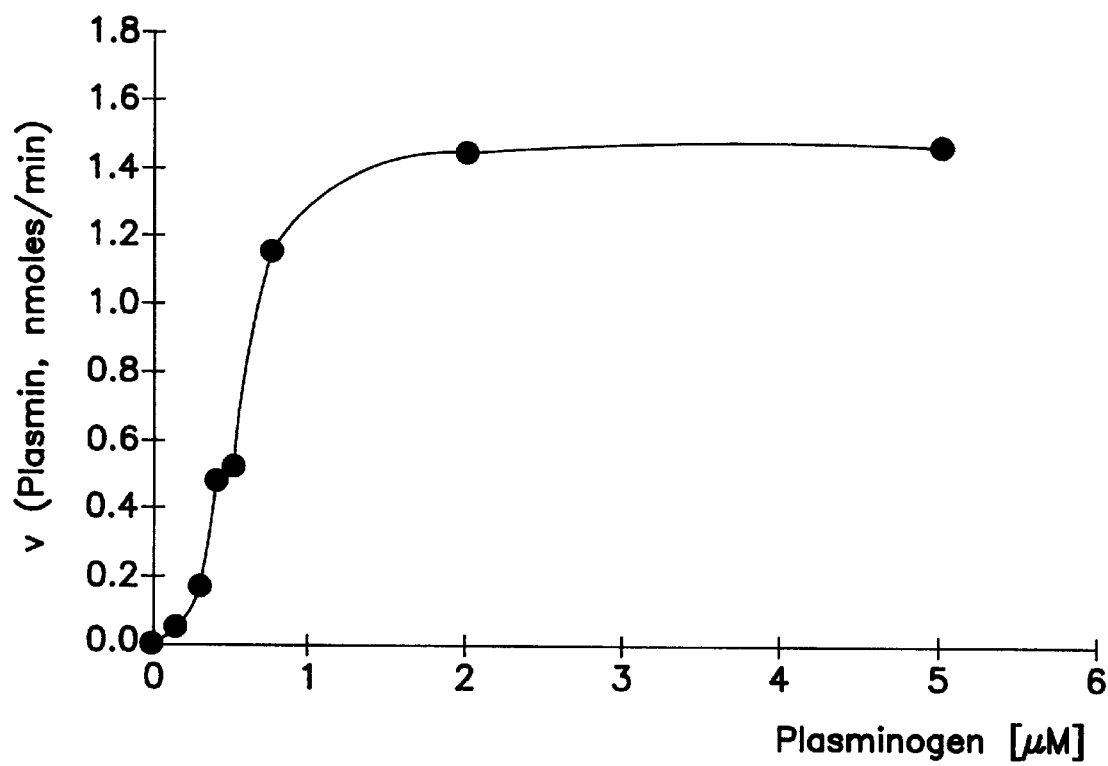
FIG. 14 represents kinetics of Glu-plasminogen activation by natural v-PA $\beta$+monomers.
Figure 14B:
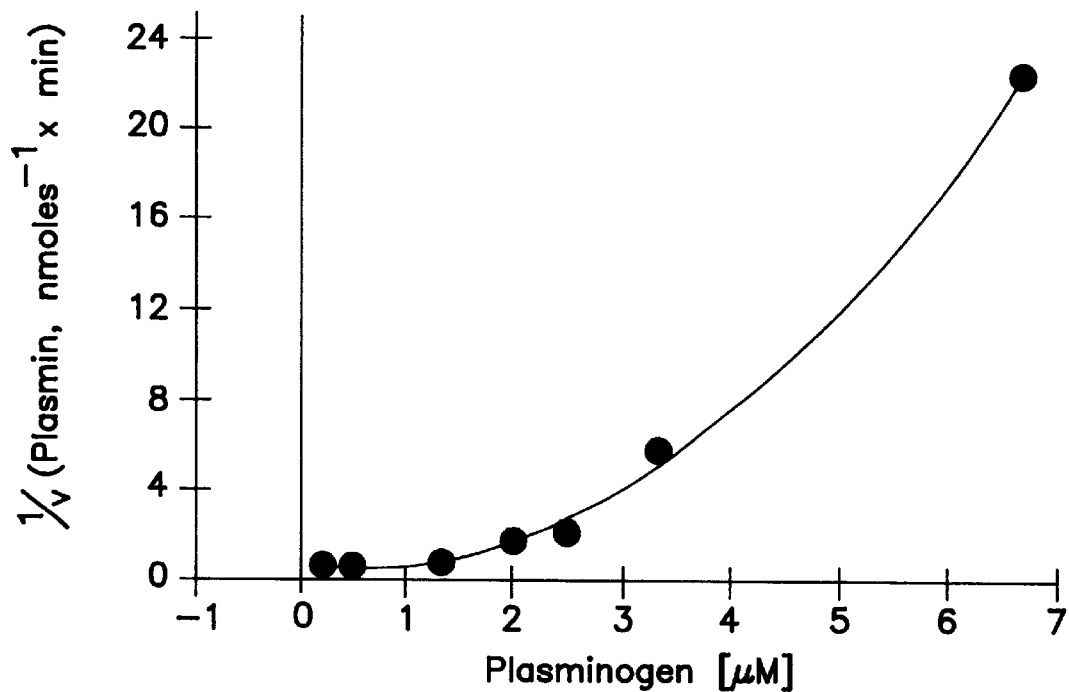
Figure 15A:
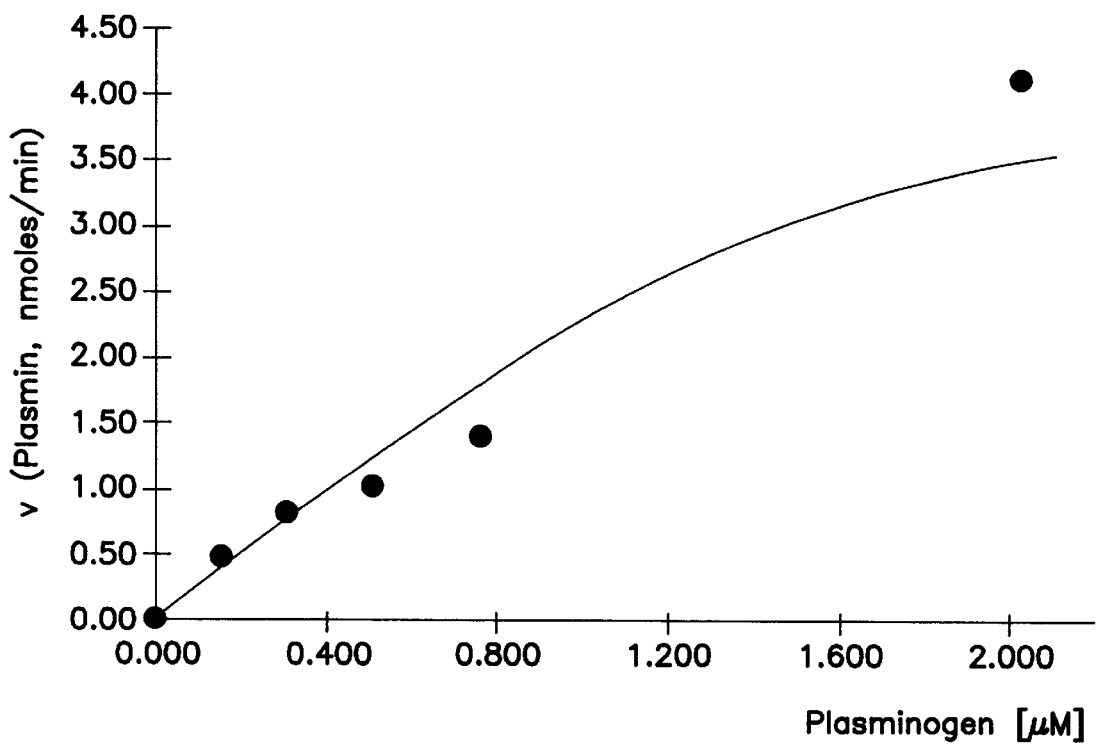
FIG. 15 represents kinetics of Glu-plasminogen activation by t-PA $\beta$+monomers.
Figure 15B:
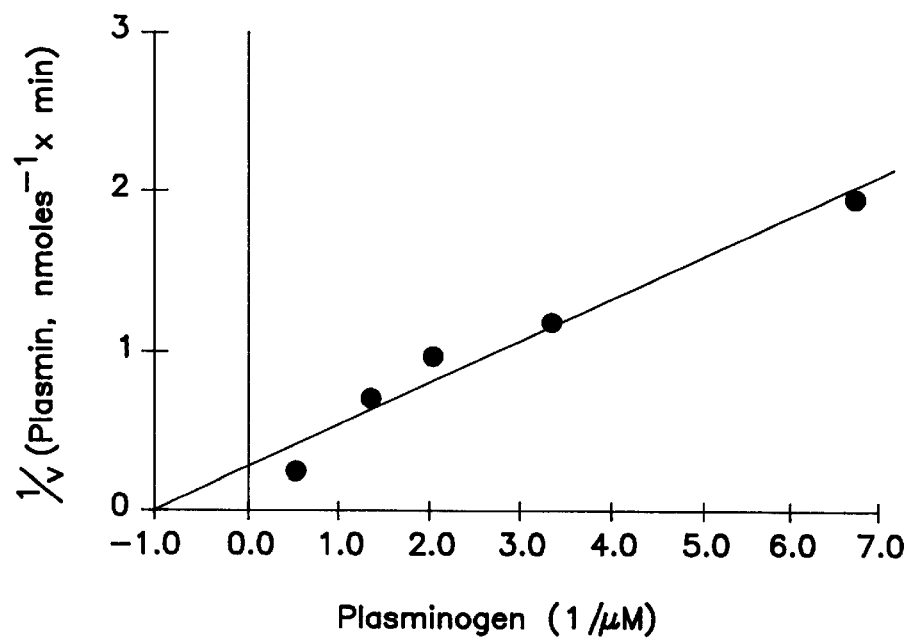

In FIG. 14 (v-PA β) and FIG. 15 (t-PA), the above-produced data are set forth. For this purpose, the plasmin formation rate v is plotted against the plasmin concentration.

In case of t-PA, a typical Michaelis Menten kinetic is obtained. When transferring these t-PA data into a Lineweaver-Burk plot (insert in FIG. 15), then a straight line is obtained.

A completely different picture is obtained when plotting the v-PA β data. The plasminogen activator v-PA β shows a different kinetic behavior from that of t-PA. The produced curve does not follow the Michaelis Menten kinetics but rather shows the typical course of an allosteric enzyme; also the Lineweaver-Burk plot shows the curve typical for an allosteric enzyme (FIG. 14).

The plasminogen activator v-PA β, in contradistinction to t-PA, is an allosteric enzyme.

Example 13
Effect of v-PA β on a Reconstituted Clot-Lyse System (International Clot-Lysis Assay)

Purified human fibrinogen is made to clot with thrombin in the presence of a constant amount of human plasminogen and various concentrations of plasminogen activator. In the thus-produced clot, the plasminogen is then converted into plasmin by the plasminogen activators; this plasmin, in turn, dissolves the fibrous substance fibrin in the clot. The time is measured between addition of thrombin and complete lysing of the clot and is plotted double-logarithmically against the plasminogen activator concentration. In accordance with the above-disclosed principle, 12.5–100 µl of a buffered solution of the purified active agent are tested and compared against 12.5–100 IU of t-PA.

Figure 16:
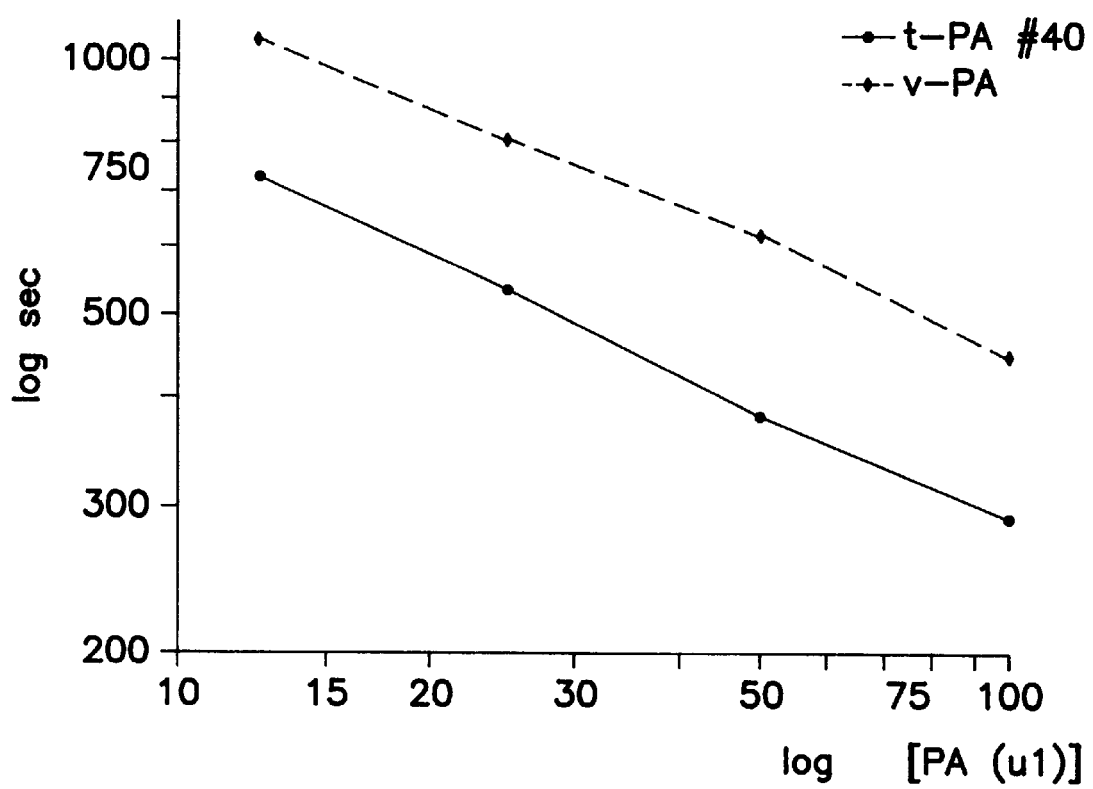
FIG. 16 represents the effect of v-PA $\beta$ on International clot-lysis assay.
Figure 17:
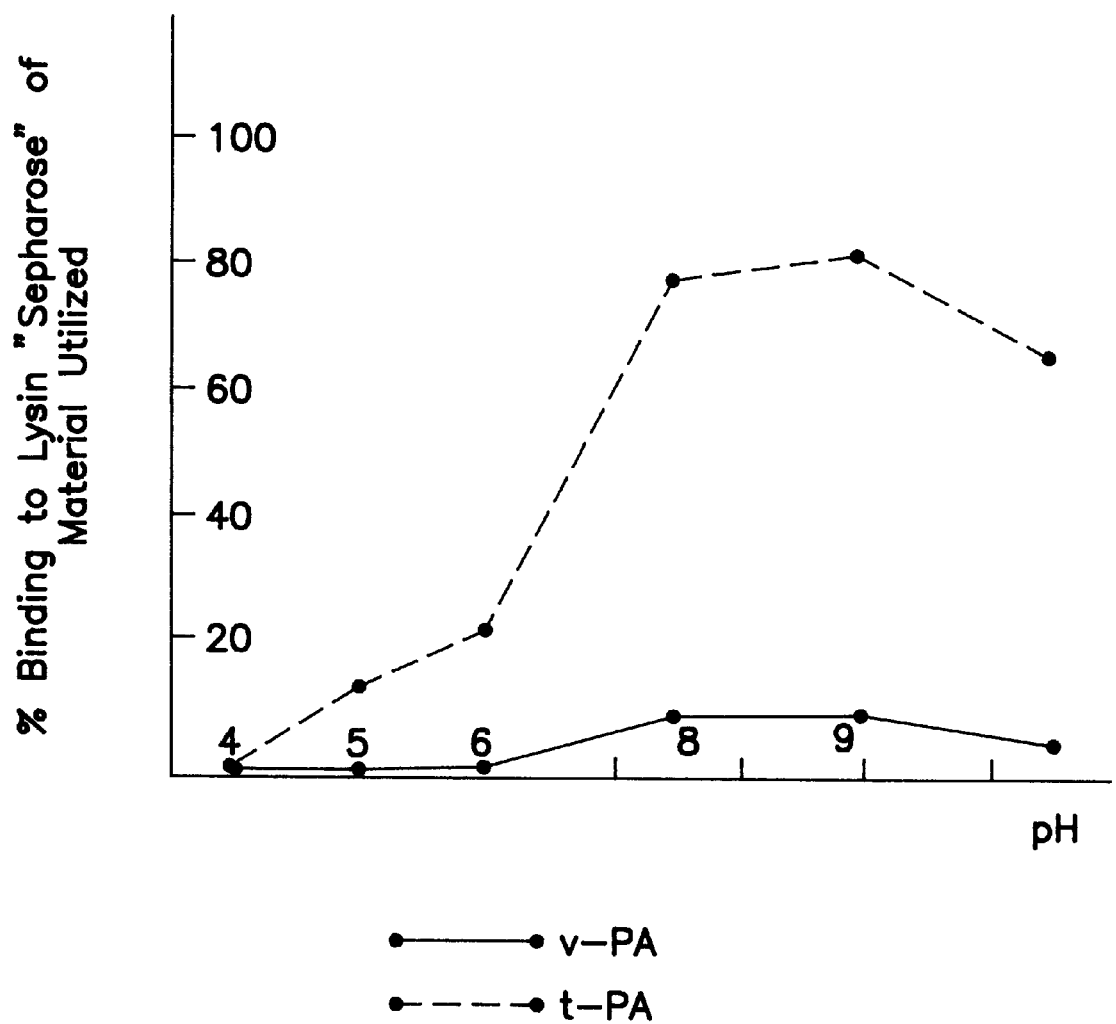
FIG. 17 represents binding of v-PA and t-PA to lysin Sepharose.
Figure 20:
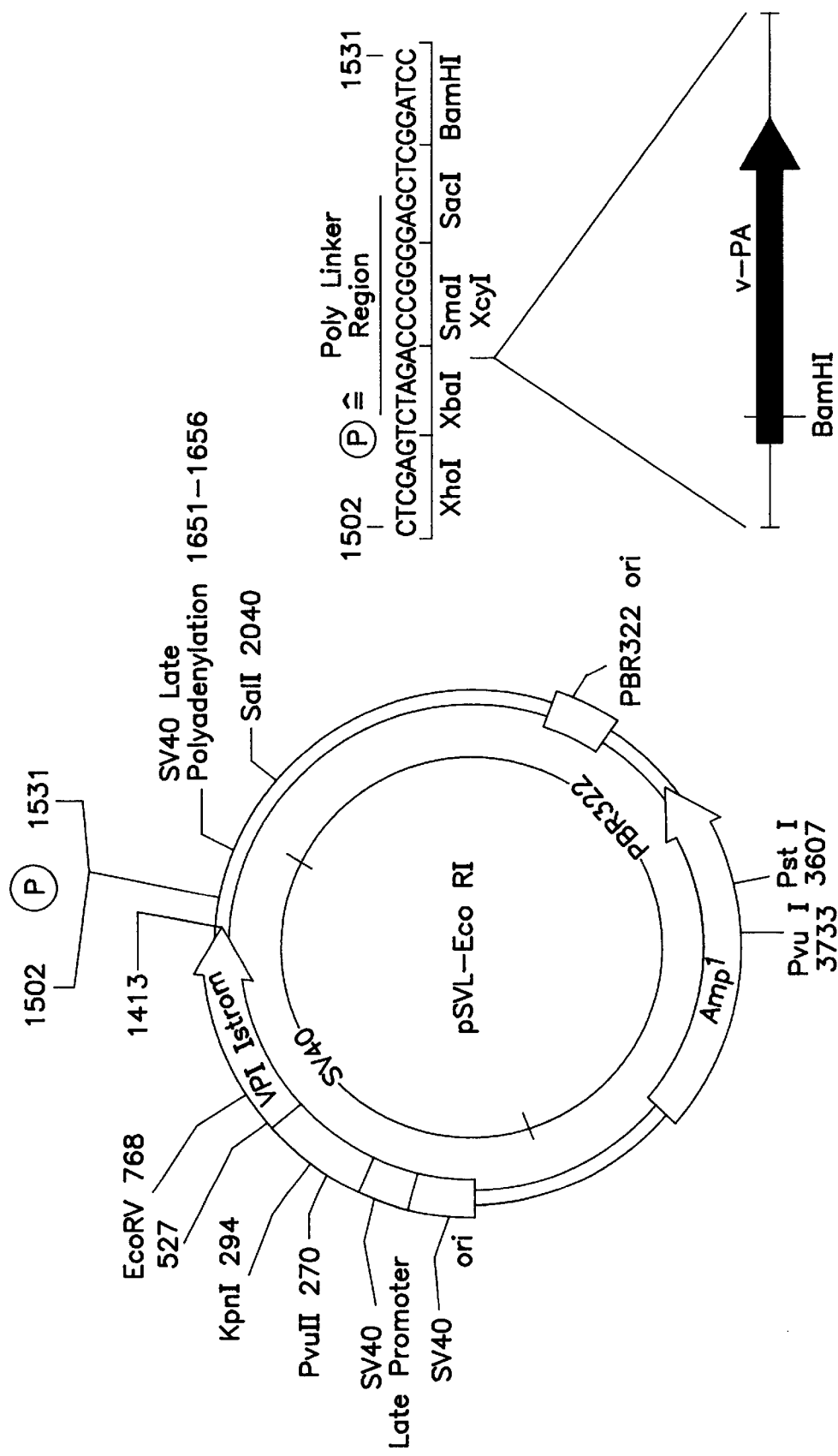
FIG. 20 represents a schematic illustration of expression vector pSVL-EcoRI with indication of the v-PA cloning site.

The result is illustrated in FIG. 16.

The novel active agent v-PA β, as compared with t-PA, results in a parallel concentration-effect curve. 100 µl of a solution of the purified active agent contains, in accordance with the test data, about 40 U of t-PA-comparable activity.

The test in detail:

Lyophilized test thrombin (Behring, Marburg) is dissolved in 1 ml of distilled water. This results in an activity of 30 IU/ml. Human plasminogen (Kabi, Munich) is dissolved in 2 mM HCl+50% glycerin+5 g/l PEG 6000. The result is an activity of 10 IU/ml. Human fibrinogen (Kabi, Munich) is brought to a concentration of 2 mg/ml of clottable protein in a phosphate buffer having the following composition: 1.605 g/l $KH_2PO_4$; 8.58 g/l $Na_2HPO_4 \cdot 2H_2O$; 100 l/l "Tween" 80; 500 mg/l HSA. The standard t-PA is diluted to an activity of 1,000 IU/ml.

20 µl of plasminogen+100 µl of thrombin are pipetted into a test tube and incubated at 37° C. 1 ml of fibrinogen and 12.5–100 µl of plasminogen activator are added simultaneously and a stopwatch is started. After 2 minutes, a glass bead (diameter 6 mm) is placed on the clot. Once the glass bead has reached the bottom of the test tube, the watch is stopped and the time is recorded.

Example 14
Binding of v-PA β and t-PA to Lysin "Sepharose" 4B

The plasmin activators are brought to the corresponding pH and treated under these conditions with the lysin "Sepharose". The lysin "Sepharose" is thoroughly washed and the activity is determined in the combined supernatants. Elution experiments could not be performed with the small amounts of v-PA.

Example 15
Caseinolysis of v-PA β and t-PA

The activity of plasminogen activators can be determined with the aid of a so-called fibrin plate test (Astrup, T., and Müllertz in Arch. Biochem. Biophys. 40 : 346–351, 1952). The plasminogen activators are incubated in pre-punched holes at 37° C. In case of the presence of plasminogen, the thus-formed plasmin will lyse the fibrin, and a lysis halo is produced, the diameter of which depends on the concentration of plasminogen activator employed. It is expected from a fibrin-specific plasminogen activator that it does not attack any other proteins besides fibrin. This can be tested by the methods described herein, replacing fibrin by casein with plasminogen (not shown).

As could be seen from the plate, v-PA β, as contrasted to t-PA, shows no lysis halos whatever on plasminogen-containing casein plates. This points to absolute fibrin specificity of v-PA β.

Example 16
Determination of the Km Value of various Amidolytic Substrates with the Plasminogen Activators t-PA, Urokinase, and the Active Forms of v-PA $\alpha_1$ and v-PA β

In a 96-hole plate, respectively 90 μl of 100 mM Tris pH 8.0/100 mM NaCl/0.01% "Tween" 80 and 50 μl of the corresponding chromogenic substrate (all from Kabi Vitrum, Stockholm, Sweden) in the final concentrations of 0.03/0.06/0.1/0.3/0.6 and 1 mM are incubated with 10 μl (3 units per hole) of the corresponding plasminogen activator at 37° C., and the thus-released p-nitroaniline is determined photometrically at 405 nm at various points in time between 0–7 hours. The resultant data are evaluated with the aid of a Lineweaver-Burk plot, and the Km value is determined (Segel, I. H., Enzyme Kinetics, John Wiley and Sons, New York). The following chromogenic substrates were utilized:

H-D-Val-Leu-Lys-pNA (S-2251)
H-D-Ile-Pro-Ars-pNA (S-2288)
<Glu-Gly-Arg-pNA (S-2444)

The following Km Values (mmol/l) were determined:

| Plasminogen Activator | S-2288 | S-2444 |
| --- | --- | --- |
| t-PA | 0.7 (1.0) | 2.0 |
| Urokinase | 0.4 (0.2) | 0.1 (0.09) |
| v-PA α1 | 1.0 | 2.0 |
| v-PA β | 2.0 | 2.0 |

The values indicated in parentheses are taken from the literature (Friedberger, P., in Scand. I. Clin. Lab. Invest. 42—Supplement 1.62, 1982).

The active agent forms of v-PA $\alpha_1$ and v-PA β show similar Km values as in case of t-PA. v-PA $\alpha_1$, v-PA β, and t-PA show no conversion whatever with the chromogenic substrate S-2251.

Example 17

Isolation and Characterization of cDNA Clones with Segments for-Plasminogen Activators from the Salivary Gland of the Vampire Bat Desmodus rotundus 1. Preparation of a cDNA Gene Bank Whole RNA from salivary glands of Desmodus rotundus is isolated according to the guanidinium isothiocyanate method [Chirgwin, J. M., Przybyla, A. E., MacDonald, R. J., Rutter, W. J., Biochemistry 18 : 5294–5299 (1979)]. From 500 μg of whole RNA, 25 μg of poly A'-RNA is isolated by oligo(dt) cellulose affinity chromatography [Aviv, H., Leder, P., Proc. Natl. Acad. Sci. USA 69 : 1408–1412 (1972)].

cDNA synthesis takes place according to the method by Gubler and Hoffmann [Gubler, U., Hoffmann, B., Gene 25: 263–269 (1983)] using the cDNA Synthex Kit of Pharmacia LKB Biotechnology AB. The individual steps take place exactly in accordance with the protocol indicated by the manufacturer. The double-strand cDNA provided with EcoRI adapters (/ microgram) is linked with the EcoRI-cut, dephosphorylated phage vector Lambda gt 10 (4 μg) with the use of T4-DNA ligase [Huynh, T. V., Young, A., Davis, R. W. in Practical Approaches in Biochemistry. DNA Cloning Volume 1, ed. Glowen, D. M., IRL Oxford, Washington, DC (1985)]. The ligase batch is packaged into infectious phages, using packaging extracts (Gigapack II Gold Packaging extracts of Stratagene, La Jolla, USA) in accordance with the protocol indicated by the manufacturer. The thus-obtained primary cDNA gene bank contains 1×10⁶ recombined lambda phages.

2. Screening of the cDNA Gene Bank with a $^{32}$P-Labeled Sequence of the cDNA Gene for the Human Tissue-Specific Plasminogen Activator (t-PA)

A t-PA cDNA sequence [Fisher, R., Waller, E. K., Grossi, G., Thompson, D., Tizard, R., and Schleuning,W.-D, J. Biol. Chem. 260 : 11223–11230 (1985)] labeled radioactively by nick translation [Maniatis, T., Fritsch, E. F., Sambrook, J., Molecular Cloning, A Laboratory Manual (Cold Spring Harbor Laboratory, New York, 1982)] serves as a probe for the identification of vampire bat saliva plasminogen activator cDNA. The DNA of, in total, 50,000 recombined lambda phages is transferred to "Replika" membranes (Gene Screen Plus, trademark of Du Pont de Nemours, NEN Research Products).

The treatment of the membranes and the composition of the hybridization solutions corresponds to the data provided by the manufacturer. The hybridization and washing temperature is 42° C. The final washing step takes place in a 4×SSC buffer. From the 50,000 screened recombined phages, 11 positive clones have been isolated.

3. Characterization of the cDNA of the Positive Clones

The cDNA insert of the positive clones is trans-cloned according to standard methods into the commercially available sequencing vectors M13 mp 18 and M13 mp 19 [Messing, J., Meth. Enzymol. 101 : 20–769 (1983)] and sequenced according to the dideoxynucleotide method [Sanger, F., Nicklen, S., Coulson, A. R., Proc. Natl. Acad. Sci. USA 74 : 5463–5467 (1977)]. Comparison of the nucleotide sequences of the individual clones with the nucleotide sequence of the cDNA gene for the human t-PA [Pennica, D., Holmes, W. E., Kohr, W. J., Harkins, R. N., Vehar, G. A., Ward, C. A., Bennet, W. F., Yelverton, E., Seeburg, P. H., Heyneker, H. L. and Goeddel, D. V., Nature 303 : 214–221 (1983)] yields a high degree of sequence identity (>80%). Also the derived protein sequences show a high sequence identity with parts of the human t-PA (>70%). None of the clones contains a cDNA for a complete vampire bat plasminogen activator gene. Partial sequences of one of these clones serve as a probe for screening a further cDNA gene bank from the salivary gland of Desmodus rotundus (Example 18).

Example 18

Isolation, Characterization and Sequencing of Complete cDNA Clones of the Plasminogen Activators from the Salivary Gland of Desmodus rotundus 1. Preparation of a cDNA Gene Bank from the Salivary Gland RNA of Desmodus rotundus A whole RNA is isolated from the salivary glands of vampire bats (D. rotundus) by digestion with guanidinium isothiocyanate and subsequent ultra-centrifuging by means of a cesium chloride cushion (1). From three milligrams of the lyophilized whole RNA, 80 μg of polyA$^+$ RNA is obtained by twice performing affinity chromatography over oligo-deoxythymidine cellulose (2, 3), Five micrograms of this preparation is utilized for cDNA synthesis according to the method by Gubler and Hoffman (4) with several modifications ("ZAP-cDNA" Synthesis Kit, Stratagene) (5, 6). The synthesis of the first strand is initiated with the aid of an oligonucleotide containing an oligo-deoxythymidine proportion and the recognition sequence of the restriction endonuclease XhoI (6), and is carried out by reverse transcriptase of Moloney murine leukemia virus with the use of 5-methyldeoxy-cytidine. The second strand is synthetized by E. coli DNA polymerase I in the presence of E. coli ribonuclease H. The ends of the thus-formed, double strand cDNA are smoothed with T4 DNA polymerase and then linked to EcoRI adapters with the use of T4 DNA ligase. The resultant DNA ends are phosphorylated with the aid of T4 polynucleotide kinase. After digestion of the cDNA with the restriction enzyme XhoI, gel filtration is performed over "Sepharose" CL-4B (Pharmacia). The fractions containing cDNA with a minimum size of 500 base pairs are combined; the yield is about 1.2 μg of cDNA. One-third of this quantity is made to link with 3 μg of the EcoRI-XhoI restriction-digested and dephosphorylated arms of the bacteriophage vector Uni-ZAP(TM)XR (patent pending) of the company Stratagene (La Jolla, USA) (5, 7). The ligation batch is packaged into seven separate batches with the use of "Giga-pack" II Gold Packaging extracts (Stratagene) (8). In this way, a primary sDNA gene bank is obtained with more than $4 \times 10^6$ recombined lambda bacteriophages.

2. Identification of cDNA Clones of the Plasminogen Activators from Vampire Bat Saliva of *Desmodus rotundus*

The probe employed for the identification of complete cDNA clones is a DNA fragment, produced by AluI-BamHI restriction digestion, of 76 base pairs in length (nucleotide 141–216 in FIG. 26*b*) from the 5'-end of a clone isolated from the first cDNA gene bank (see Example 17). This fragment is labeled radioactively by nick translation (9) in the presence of [α-$^{32}$P] deoxyadenosine triphosphate and utilized for the hybridization of replica filters on which DNA of, in total, $1.2 \times 10^5$ recombinant bacteriophages of the primary cDNA gene bank has been immobilized (10). Hybridization and washing temperature is 50° C. The final washing step takes place in 2×SSC buffer (10). Of more than 200 clones that have emitted a signal in the autoradiography of the "Replika" filters, 50 clones are purified by separate plating out and repetition of the aforedescribed plaque filter hybridization. In this way, 38 clones are isolated which also in the second screening yield a clearly positive signal.

3. Characterization and Sequencing of the cDNA Clones

The plasmid pBluescript SK, contained in the isolated positive UnitZAP(TM)XR bacteriophage clones—inclusive of the cDNA fragment integrated in the same segment of the bacteriophage—is removed from the bacteriophages by so-called "in vivo excision" (7, 14), thus obtaining in total 35 different pBluescript SK plasmid clones stemming from the positive bacteriophage clones. The plasmids are isolated in accordance with the method by Birnboim and Doly (11), and their cDNA proportion is divided into four different classes $\alpha_1$, $\alpha_2$, β, γ, in accordance with restriction analysis with the enzymes BamHI and PstI (results not shown) and DNA sequencing of the 5'-ends. The results showed a restriction pattern of selected pBluescript SK plasmid clones with the respectively longest cDNA proportions from the four groups of $\alpha_1$ (2 plasmid clones), $\alpha_2$ (1 plasmid clone), β (4 plasmid clones) and γ (1 plasmid clone), wherein the plasmid DNA preparations, digested with the restriction enzymes BamHI ("B"), PstI ("P") or a mixture of these two restriction enzymes ("BP") were separated on a 1.8% agarose gel, the yardstick regarding size was represented by plasmid pBR322 ("M", DNA molecular weight marker 5 of the company Boehring-Mannheim) digested with the restriction enzyme HaeIII, the size of the clearly visible fragments is 587, 540, 504, 458, 434, 267, 234, 213, 192, to 184, and 123 base pairs (from the top toward the bottom) and the agarose gel was colored with ethidium bromide after electrophoretic separation and photographed; from the groups $\alpha_1$ and β the left most pictured clones were sequenced, respectively. The cDNA proportions of the longest cDNA clones of all four classes are subcloned into the bacteriophage vectors M13mp19 (12) and sequenced with the dideoxy-nucleotide method by Sanger ("Sequenase" kit, United States Biochemical Corporation, Cleveland, USA) (13, 15) (using, in part, oligonucleotide primers which are synthesized specifically for this purpose and are complementary to sequences of the cDNA proportions). The complete cDNA sequences (including a short segment of the polyA chains present at the 3'-end) with the thus-derived protein sequences are represented in FIGS. 18A–D.

1. Chirgwin, J. M., Przybyla, A. E., MacDonald, R. J. Rutter, W. J., Biochemistry 18, 52–94–5299 (1979).
2. Schwab, M., Alitalo, K., Varmus, H. E., Bishop, J. M., Nature 303, 497–501 (1983).
3. Pharmacia LKB Biotechnology AB, mRNA Purification Kit—Instructions, 1–16 (no year given)
4. Gubler, U., Hoffman, B., Gene 25, 263–269 (1963).
5. Huse, W. D., Hansen, C. Strategies 1, 1–3 (1989).
6. Firma Stratagene, ZAP-cDNA-(TM)Synthesis Kit—Instruction Manual, 1–21 (1989).
7. Firma Stratagene, Uni-ZAP(TM)XR Cloning Kit—Instruction Manual, 1–11 (1989).
8. Firma Stratagene, Gigapack II Gold Packaging Extract—Instruction Manual, 1–5 (1989)
9. Maniatis, T. Fritsch, E. F., Sambrook, J., Molecular Cloning, A Laboratory Manual (Cold Spring Harbor Laboratory, New York, (1982)
10. Du Pont de Nemours, NEN Research Products, Colony/PlaqueScreen, Hybridization Transfer Membrane—Directions, 1–11 (no year)
11. Birnboim, H. C., Doly, J., Nucleic Acids Res. 7, 1513–1523 (1979).
12. Messing. J., Meth. Enzymol. 101, 20–79 (1983).
13. Sanger, F., Nicklen, S., Coulson, A. R., Proc. Natl. Acad. Sci. USA 74, 5463–5467 (1977).
14. Short, J. M., Fernandez, J. M. Sorge, J. M., Huse, W. D., Nucleic Acids Res. 16, 7583–7600 (1988).
15. Unites States Biochemical Corporation, Step-By-Step Protocols For DNA Sequencing with Sequenase Version 2.0, 1–21 (1988).

Example 19

Construction of Expression Vectors Containing the Coding sequences of the Active Agent v-PA, and Testing of Same by Microinjection into Oocytes The coding sequences from the cDNA clones of the v-PA forms $\alpha_1$, $\alpha_2$, β, and γ are obtained by cleavage with the restriction endonuclease EcoRI and, after treatment with the Klenow fragment of *E. coli* DNA polymerase I, and isolation from low melting temperatur agarose gels, linked into the XbaI site of the vector pSVL-EcoRI filled up by the Klenow fragment of *E. coli* DNA polymerse I and treated with calf intestine phosphatase (Boehringer Mannheim). The correct orientation is tested with BamRI. The pSVL-EcoRl involves a derivative of the commercially available SV40 expression plaemid pSVL (Pharmacia).

The thus-produced expression vectors are purified over a cesium chloride gradient and utilized for microinjection into *Xenopus laevis* oocytes.

Oocyte injection was performed according to the following cited articles:

1. Gurdon, J. B., and Wakefield, L., in "Microinjection and Organelle Transplantation Techniques", eds. Celis, J. E., Graessmann, A., and Loyter, A., Academic Press, London, 1986.
2. Colman, A., in "Transcription and Translation—A Practical Approach", eds. Hames, R. J., and Higgins, S. J., IRL-Press Oxford, 1984.
3. Langer, G., "Analyse des Drosophila U1 SURNA Promotors in homologen in vitro und heterologen in vitro Transkriptionssystemen", Ph.D.Thesis, University of Kaiserslautern, 1987.

After embedding the oocytes, injected with the v-PA expression vectors, in a fibrin plate prepared with Barth medium (literature 2), lysis halos are produced. When using, in place of the fibrin plate, a casein plate, then no lysis takes place ($\alpha_1$, $\alpha_2$, β). Oocytes injected with a vector not containing the v-PA sequence do not exhibit a lysis halo.

The v-PA cDNA sequences contain a functional signal paptide sequence responsible for the export of the v-PA protein out of the cell.

These results clearly show that the thus-obtained v-PA cDNA clones are complete and, after incorporation into a suitable expression vector, produce active effective agent which is absolute fibrin-specific.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An isolated plasminogen activator having the amino acid sequence

```
                        M V N T M K T K L
    L C V L L L C G A V F S L P R Q E T Y R
    Q L A R G S R A Y G V A C K D E I T Q M
    T Y R R Q E S W L R P E V R S K R V E H
    C Q C D R G Q A R C H T V P V N S C S E
    P R C F N G G T C W Q A V Y F S D F V C
    Q C P A G Y T G K R C E V D T R A T C Y
    E G Q G V T Y R G T W S T A E S R V E C
    I N W N S S L L T R R T Y N G R M P D A
    F N L G L G N H N Y C R N P N G A P K P
    W C Y V I K A G K F T S E S C S V P V C
    S K A T C G L R K Y K E P Q L H S T G G
    L F T D I T S H P W Q A A I F A Q N R R
    S S G E R F L C G G I L I S S C W V L T
    A A H C F Q E S Y L P D Q L K V V L G R
    T Y R V K P G E E E Q T F K V K K Y I V
    H K E F D D D T Y N N D I A L L Q L K S
    D S P Q C A Q E S D S V R A I C L P E A
    N L Q L P D W T E C E L S G Y G K H K S
    S S P F Y S E Q L K E G H V R L Y P S S
    R C A P K F L F N K T V T N N M L C A G
    D T R S G E I Y P N V H D A C Q G D S G
    G P L V C M N D N H M T L L G I I S W G
    V G C G E K D V P G V Y T K V T N Y L G
    W I R D N M H L
``` or a glycosylated or microheterogenous form thereof.

2. An isolated plasminogen activator having the amino acid sequence

```
                        A Y G V A C K D E I T Q M
    T Y R R Q E S W L R P E V R S K R V E H
    C Q C D R G Q A R C H T V P V N S C S E
    P R C F N G G T C W Q A V Y F S D F V C
    Q C P A G Y T G K R C E V D T R A T C Y
    E G Q G V T Y R G T W S T A E S R V E C
    I N W N S S L L T R R T Y N G R M P D A
    F N L G L G N H N Y C R N P N G A P K P
    W C Y V I K A G K F T S E S C S V P V C
```

-continued

```
    S K A T C G L R K Y K E P Q L H S T G G
    L F T D I T S H P W Q A A I F A Q N R R
    S S G E R F L C G G I L I S S C W V L T
    A A H C F Q E S Y L P D Q L K V V L G R
    T Y R V K P G E E E Q T F K V K K Y I V
    H K E F D D D T Y N N D I A L L Q L K S
    D S P Q C A Q E S D S V R A I C L P E A
    N L Q L P D W T E C E L S G Y G K H K S
    S S P F Y S E Q L K E G H V R L Y P S S
    R C A P K F L F N K T V T N N M L C A G
    D T R S G E I Y P N V H D A C Q G D S G
    G P L V C M N D N H M T L L G I I S W G
    V G C G E K D V P G V Y T K V T N Y L G
    W I R D N M H L
``` or a glycosylated or microheterogeneous form thereof.

3. A plasminogen activator of claim 1, which is recombinantly produced.

4. An allelic variant of a plasminogen activator of claim 3.

5. A pharmaceutical preparation comprising a plasminogen activator of claim 3 and a pharmaceutically acceptable excipient.

6. An isolated DNA molecule encoding a polypeptide having the amino acid sequence of a plasminogen activator of claim 1.

7. An isolated DNA molecule encoding a polypeptide having the amino acid sequence of a plasminogen activator of claim 4.

8. A. A replicable cloning vector comprising a DNA molecule of claim 6.

9. An expression vector comprising a DNA molecule of claim 6.

10. A microorganism transformed with a vector of claim 8.

11. A microorganism host cell transformed with a vector of claim 9.

12. A eukaryotic host cell transformed with a vector of claim 9.

13. A mammalian host cell transformed with a vector of claim 9.

14. A method of producing a plasminogen activator, comprising
    culturing a host cell transformed with a DNA molecule of claim 6 under conditions whereby said DNA molecule is expressed; and
    isolating the thus-produced plasminogen activator.

15. A plasminogen activator of claim 1, which is free of other bat proteins.

* * * * *